(12) United States Patent
Kim et al.

(10) Patent No.: US 9,927,720 B2
(45) Date of Patent: Mar. 27, 2018

(54) SUBSTRATE TARGET FOR IN-SITU LITHOGRAPHY METROLOGY, METROLOGY METHOD FOR IN-SITU LITHOGRAPHY, AND METHOD OF MANUFACTURING INTEGRATED CIRCUIT DEVICE BY USING IN-SITU METROLOGY

(71) Applicant: Samsung Electronics Co., Ltd., Suwon-Si, Gyeonggi-do (KR)

(72) Inventors: Ji-myung Kim, Hwaseong-si (KR); Gyu-min Jeong, Ulsan (KR); Tae-hwa Jeong, Hwaseong-si (KR); Kwang-sub Yoon, Yongin-si (KR)

(73) Assignee: Samsung Electronics Co., Ltd. (KR)

( * ) Notice: Subject to any disclaimer, the term of this patent is extended or adjusted under 35 U.S.C. 154(b) by 242 days.

(21) Appl. No.: 14/728,529

(22) Filed: Jun. 2, 2015

(65) Prior Publication Data

US 2016/0033398 A1 Feb. 4, 2016

(30) Foreign Application Priority Data

Jul. 29, 2014 (KR) ........................ 10-2014-0096767

(51) Int. Cl.
*G03F 7/20* (2006.01)
*H01L 23/544* (2006.01)
(Continued)

(52) U.S. Cl.
CPC ...... *G03F 7/70683* (2013.01); *G01B 11/0641* (2013.01); *G03F 7/70625* (2013.01);
(Continued)

(58) Field of Classification Search
CPC .. G01N 21/93; G01N 21/956; G01N 21/9507; G01N 21/95684; G01N 21/95692; G01N 21/9501; G01N 2201/02; G01N 21/21; G01N 21/211; G01N 21/4788; G01N 21/55; G03F 7/70625; G03F 7/70633;
(Continued)

(56) References Cited

U.S. PATENT DOCUMENTS 5,300,786 A 5/1994 Brunner et al.
6,426,837 B1 7/2002 Clark et al.
(Continued)

FOREIGN PATENT DOCUMENTS

CN 101435997 A 5/2009
CN 103777467 A 5/2014
(Continued)

OTHER PUBLICATIONS

Minhas, Babar K. et al., "Ellipsometric scatterometry for the metrology of sub-0.1-μm-linewidth structures," 1998, Applied Optics, vol. 37, No. 22, pp. 5112-5115.*
(Continued)

*Primary Examiner* — Gordon J Stock, Jr.
(74) *Attorney, Agent, or Firm* — Ward and Smith, P.A.

(57) ABSTRACT

A substrate can include a feature pattern included in an integrated circuit on the substrate and an in-situ metrology pattern spaced apart from the feature pattern on the substrate, the in-situ metrology pattern and the feature pattern both configured to have equal heights relative to a surface of the substrate.

17 Claims, 20 Drawing Sheets

(51) Int. Cl.
  *G01B 11/06* (2006.01)
  *G01N 21/956* (2006.01)
  *G01N 21/93* (2006.01)

(52) U.S. Cl.
  CPC ...... *G03F 7/70633* (2013.01); *G03F 7/70641* (2013.01); *H01L 23/544* (2013.01); *G01N 21/93* (2013.01); *G01N 21/956* (2013.01)

(58) Field of Classification Search
  CPC ............ G03F 7/70641; G03F 7/70683; G03F 7/70616; G03F 7/7065; G01B 11/02; G01B 11/06; G01B 11/0608; G01B 11/0616; G01B 11/0641; G01B 11/065; G01B 11/22; H01L 23/544
  See application file for complete search history.

(56) References Cited

U.S. PATENT DOCUMENTS

| | | | |
|---|---|---|---|
| 6,710,853 B1 | 3/2004 | La Fontaine et al. | |
| 7,867,692 B2 | 1/2011 | Amako et al. | |
| 8,320,226 B2 | 11/2012 | Hirai | |
| 8,830,585 B2 | 9/2014 | Hirai et al. | |
| 2006/0183040 A1* | 8/2006 | Sasazawa | G03F 7/70641 430/30 |
| 2006/0234136 A1* | 10/2006 | Kim | G03F 9/7026 430/5 |
| 2007/0201043 A1* | 8/2007 | Raymond | G01B 11/00 356/625 |
| 2008/0311344 A1* | 12/2008 | Marie Kiers | G01N 21/4788 428/138 |
| 2010/0209830 A1* | 8/2010 | Carcasi | G03F 7/70625 430/30 |
| 2011/0003256 A1* | 1/2011 | Van Der Heijden et al. | G03F 7/70466 430/324 |
| 2011/0229830 A1* | 9/2011 | Bhattacharyya | G03F 7/70625 430/325 |
| 2012/0314292 A1* | 12/2012 | Mathai | G02B 5/1819 359/575 |
| 2013/0314784 A1 | 11/2013 | Fattal et al. | |
| 2014/0029104 A1 | 1/2014 | Guo et al. | |

FOREIGN PATENT DOCUMENTS

| | | |
|---|---|---|
| JP | 2008-241879 | 10/2008 |
| JP | 2008-276823 | 11/2008 |
| JP | 2010-164749 | 7/2010 |
| JP | 2010-261999 | 11/2010 |
| KR | 1020100085595 | 7/2010 |

OTHER PUBLICATIONS

Murnane, Michael R. et al., "Subwavelength photoresist grating metrology using scatterometry," 1995, SPIE, vol. 2532, pp. 251-261.*

Brunner et al., *Quantitative Stepper Metrology using the Focus Monitor Test Mask*, IBM Semiconductor Research and Development Center, SPI vol. 2197, Jun. 9, 2014, pp. 541-549.

Fontaine et al., *Analysis of Focus Errors in Lithography using Phase-Shift Monitors*, Optical Microlithography XV, Proceedings of SPIE vol. 4691 (2002), pp. 315-324.

Hiroshi Nomura, *New Phase Shift Gratings for Measuring Aberrations*, Optical Microlithography XIV, Proceedings of SPIE Vo. 4346 (2001), pp. 25-35.

Richter et al., *Design Considerations of Form Birefringent Microstructures*, Applied Optics, vol. 34, No. 14, May 10, 1995, pp. 2421-2429.

* cited by examiner

SUBSTRATE TARGET FOR IN-SITU LITHOGRAPHY METROLOGY, METROLOGY METHOD FOR IN-SITU LITHOGRAPHY, AND METHOD OF MANUFACTURING INTEGRATED CIRCUIT DEVICE BY USING IN-SITU METROLOGY

CROSS-REFERENCE TO RELATED APPLICATIONS

This application claims the benefit of Korean Patent Application No. 10-2014-0096767, filed on Jul. 29, 2014, in the Korean Intellectual Property Office, the disclosure of which is incorporated herein in its entirety by reference.

FIELD

The inventive concept relates to lithography metrology, and more particularly to lithography metrology used for the formation of integrated circuits.

BACKGROUND

Recently, with increasing integration densities of semiconductor devices, various photolithography techniques for forming fine patterns have been developed. Various metrology techniques have also been proposed to monitor a photolithographic process in order to manufacture highly-integrated devices. As integration densities of semiconductor devices increase, a critical dimension (CD) of a photoresist pattern decreases.

Examples of approaches to measuring focal variation generated in exposure equipment include focus exposure matrix (FEM), phase shift focus monitoring (PSFM), and phase grating focus monitoring (PGFM). In the FEM approach, a human evaluates a critical dimension (CD) of patterns and an image according to a constant variation of a focus and a dose for an exposure process by using scanning electron microscope (SEM) measuring equipment in order to determine a focal variation. Thus, the elapsed time from measurement to analysis can be excessive, and the analysis may be subjective. The PSFM and PGFM approaches both can use identical types of masks and identical measuring principles and methods.

SUMMARY

The inventive concept can provide a substrate target for lithography metrology capable of being used in more precise in-line monitoring of minute focal variations that accompany a lithographic process performed to manufacture an integrated circuit (IC) device.

The inventive concept can also provide a lithography metrology method and a lithography metrology apparatus capable of more precise and non-destructive in-line monitoring of minute focal variations that accompany a lithographic process performed to manufacture an IC device, without adding a separate process to a process of manufacturing the IC device.

The inventive concept can also provide a method of manufacturing an IC device, in which the critical dimension (CD) uniformity of patterns used in manufacturing an IC device may be improved and a more reliable IC device may be manufactured, by using the lithography metrology method capable of more precise and non-destructive in-line monitoring of minute focal variations that accompany a lithographic process performed to manufacture an IC device.

In some embodiments according to the inventive concept, a substrate target for lithography metrology can include a substrate having a feature pattern on the substrate. A Sub-Wavelength Grating (SWG) key can be on a same level relative to the substrate as the feature pattern, where the SWG key can include a plurality of diffraction patterns spaced apart at a first pitch that is configured to measure a focal variation affecting formation of the feature pattern.

In some embodiments according to the inventive concept, the SWG key and the feature pattern can be the same material. In some embodiments according to the inventive concept, the first pitch is less than a wavelength of a radiation beam used to measure the focal variation. In some embodiments according to the inventive concept, each of the diffraction patterns has a rectangular cross-sectional shape. In some embodiments according to the inventive concept, each of the diffraction patterns has inclined sidewalls.

In some embodiments according to the inventive concept, a substrate target for lithography metrology can include a micro-Diffraction Based Overlay (micro-DBO) key on a substrate, where the micro-DBO key can include a plurality of first diffraction patterns each having a first width as a minimum width and a Sub Wavelength Grating (SWG) key on the substrate, where the SWG key can include a plurality of second diffraction patterns each having a width that is less than the first width.

In some embodiments according to the inventive concept, the micro-DBO key is located within a first area on the substrate and the SWG key is located in a second area of the substrate within the first area and is surrounded by the plurality of first diffraction patterns. In some embodiments according to the inventive concept, the micro-DBO key can be configured to measure an overlay error of a plurality of feature patterns on the substrate, and the SWG key can be configured to measure a focal variation affecting formation of the plurality of feature patterns.

In some embodiments according to the inventive concept, the second diffraction patterns have respective line shapes that are parallel to each other and the second diffraction patterns and the feature patterns are the same material.

In some embodiments according to the inventive concept, a lithography metrology apparatus can include a stage configured to support a target substrate. An illumination device can be configured to generate a radiation beam having a width that is greater than a first pitch. A projection device can include a polarizer configured to polarize the radiation beam such that the radiation beam is configured to impinge on the target substrate. A detection device can include a first detection unit configured to detect data about a transverse electric (TE) polarized light component and a transverse magnetic (TM) polarized light component from a zero-order diffracted light beam from among output beams diffracted by the target substrate. A data storage device can include a first storage medium configured to store first data about defocus determined to have occurred during lithography, based on the data about the TE polarized light component and the TM polarized light component. A determination device can include a first determination unit configured to determine a focal variation from the data detected by the detection device, based on the first data stored in the data storage device.

In some embodiments according to the inventive concept, the first detection unit can be configured to detect a phase difference between the TE polarized light component and the TM polarized light component and the first data can be associated with defocus that is determined based on the phase difference. In some embodiments according to the inventive concept, the target substrate can be configured to include a plurality of feature patterns and a SubWavelength Grating (SWG) key can include a plurality of diffraction patterns spaced apart at the first pitch via lithography by an exposure apparatus where the focal variation occurs during formation of the plurality of feature patterns on the target substrate.

In some embodiments according to the inventive concept, the projection device can be configured to project the radiation beam to the target substrate in a direction perpendicular to a direction in which the target substrate extends. In some embodiments according to the inventive concept, the projection device can be configured to project the radiation beam to impinge onto the target substrate within an angle range of ±89° with respect to a direction perpendicular to a direction in which the target substrate extends.

In some embodiments according to the inventive concept, the apparatus can further include a control device configured to determine compensated focus data based on the focal variation. In some embodiments according to the inventive concept, the data storage device can further include a second storage medium configured to store second data including a depth of focus (DOF), including a tolerance of defocus determined to have occurred during an exposure of the target substrate. The determination device can further include a second determination unit configured to transmit a target substrate rework command to the control device when the defocus deviates from the DOF.

In some embodiments according to the inventive concept, the target substrate can further include a micro-Diffraction Based Overlay (DBO) key formed simultaneously with the SWG key, the micro-DBO key can include diffraction patterns spaced apart on the target substrate at a pitch that is greater than the first pitch, where the detection device can further include a second detection unit configured to detect data about ±n-order diffracted light beams diffracted at respective angles so as to be symmetrical with each other about a zero-order diffracted light beam from among output beams diffracted by the micro-DBO key, wherein n is an integer equal to or greater than 1. The determination device can further include a second determination unit configured to determine an overlay error of the plurality of feature patterns from the data about the ±n-order diffracted light beams.

In some embodiments according to the inventive concept, the micro-DBO key and the SWG key can be located within a one-time measurement spot formed by a single shot radiation beam projected onto the target substrate by the projection device. In some embodiments according to the inventive concept, the second determination unit can be configured to determine the overlay error of the plurality of feature patterns from an intensity deviation between ±1-order diffracted light beams.

In some embodiments according to the inventive concept, the projection device can be configured to project polarized light obtained from at least two types of radiation beams onto the target substrate when the target substrate is stationary. In some embodiments according to the inventive concept, the at least two types of radiation beams have different wavelengths that are simultaneously incident on an identical location on the target substrate.

In some embodiments according to the inventive concept, the at least two types of radiation beams are sequentially incident upon an identical location on the target substrate. In some embodiments according to the inventive concept, the at least two types of radiation beams have identical wavelengths.

In some embodiments according to the inventive concept, a lithography metrology method can be provided by forming, on a same level on a target substrate via lithography, a plurality of diffraction patterns spaced apart at a first pitch and a plurality of feature patterns. A radiation beam can be impinged onto the plurality of diffraction patterns, the radiation beam having a wavelength that is greater than the first pitch. Data can be detected about a TE polarized light component and a TM polarized light component from a zero-order diffracted light beam from among output beams diffracted by the plurality of diffraction patterns in response to the radiation beam and a focal variation affecting formation of the plurality of feature patterns during the lithography can be detected, based on the data about the TE polarized light component and the TM polarized light component.

In some embodiments according to the inventive concept, impinging a radiation beam can include impinging polarized light onto the target substrate within an angle range of ±89° with respect to a direction perpendicular to a direction in which the target substrate extends. In some embodiments according to the inventive concept, detecting data about a TE polarized light component and a TM polarized light component can include detecting a phase difference between the TE polarized light component and the TM polarized light component and determining a focal variation can include determining a height of each of the plurality of diffraction patterns based on the phase difference and determining the focal variation based on the height of each of the plurality of diffraction patterns.

In some embodiments according to the inventive concept, the method can further include detecting data about ±n-order diffracted light beams diffracted at angles so as to be symmetrical with each other about the zero-order diffracted light beam from among the output beams diffracted by the plurality of diffraction patterns, wherein n is an integer equal to or greater than 1 and determining an overlay error of the plurality of feature patterns based on the data about the ±n-order diffracted light beams.

In some embodiments according to the inventive concept, detecting the data about the ±n-order diffracted light beams can include simultaneously detecting the data about the ±n-order diffracted light beams with detecting the data about the TE polarized light component and the TM polarized light component. In some embodiments according to the inventive concept, determining the overlay error can include determining the overlay error simultaneously with determining the focal variation.

In some embodiments according to the inventive concept, impinging the radiation beam can include radiating a first radiation beam having a width that is greater than the first pitch and radiating a second radiation beam to be incident on a same location on the substrate as a location on which the first radiation beam is incident. In some embodiments according to the inventive concept, detecting data can include determining the focal variation from a phase difference between a TE polarized light component and a TM polarized light component of a zero-order diffracted light beam from among output beams obtained by the plurality of diffraction patterns diffracting the first radiation beam and determining an overlay error of the plurality of feature patterns from an intensity deviation between ±n-order diffracted light beams diffracted at angles so as to be symmetrical with each other from among output beams obtained by the plurality of diffraction patterns diffracting the second radiation beam, wherein n is an integer equal to or greater than 1.

In some embodiments according to the inventive concept, a method of manufacturing an integrated circuit (IC) device can be provided by forming a photoresist layer on a substrate and exposing the photoresist layer by applying a first focus set value, and by simultaneously forming, on a same level on the substrate a feature pattern, and a SubWavelength Grating (SWG) key including a plurality of diffraction patterns spaced apart at a first pitch on the substrate by developing the exposed photoresist layer. A radiation beam having a wavelength that is greater than the first pitch can be impinged onto the plurality of diffraction patterns. Data about a TE polarized light component and a TM polarized light component can be detected from a zero-order diffracted light beam from among output beams diffracted by the plurality of diffraction patterns. A focal variation affecting the formation of the feature pattern can be determined based on the data about the TE polarized light component and the TM polarized light component and whether the first focus set value is to be corrected can be determined, based on the focal variation.

In some embodiments according to the inventive concept, detecting data can include detecting a phase difference between the TE polarized light component and the TM polarized light component and determining a focal variation can include determining a height of each of the plurality of diffraction patterns based on the phase difference and determining actual focus applied in the exposing of the photoresist layer, based on the height of each of the plurality of diffraction patterns.

In some embodiments according to the inventive concept, detecting data can include detecting the phase difference between the TE polarized light component and the TM polarized light component from a zero-order diffracted light beam which is an output beam diffracted by the plurality of diffraction patterns and determining the focal variation comprises determining a focal variation affecting formation of the feature pattern, based on the phase difference between the TE polarized light component and the TM polarized light component.

In some embodiments according to the inventive concept, simultaneously forming, on a same level on the substrate a feature pattern, and a SubWavelength Grating (SWG) key can include forming a micro-DBO key including a plurality of additional diffraction patterns having a second pitch that is greater than the first pitch, simultaneously with the feature pattern and the SWG key, and detecting data can include detecting the phase difference between the TE polarized light component and the TM polarized light component from a zero-order diffracted light beam from among output beams that are reflected and diffracted by the plurality of diffraction patterns. Intensities of ±n-order diffracted light beams diffracted at angles can be detected so as to be symmetrical with each other from among output beams that are reflected and diffracted by the plurality of additional diffraction patterns, wherein n is an integer equal to or greater than 1.

In some embodiments according to the inventive concept, the method can further include determining an overlay error of the feature pattern from the detected intensities of the ±n-order diffracted light beams. In some embodiments according to the inventive concept, the radiation beam has a wavelength of about 230 to about 850 nm.

In some embodiments according to the inventive concept, a substrate can include a feature pattern included in an integrated circuit on the substrate and an in-situ metrology pattern spaced apart from the feature pattern on the substrate, the in-situ metrology pattern and the feature pattern both configured to have equal heights relative to a surface of the substrate.

In some embodiments according to the inventive concept, the in-situ metrology pattern and the feature pattern are both lithographically configured to have the equal heights relative to the surface of the substrate. In some embodiments according to the inventive concept, the in-situ metrology pattern and the feature pattern are commonly formed on the substrate.

In some embodiments according to the inventive concept, the in-situ metrology pattern can include a SubWavelength Grating (SWG) key including a plurality of diffraction patterns spaced apart at a first pitch on the substrate that is configured to measure focal variation affecting formation of the feature pattern. In some embodiments according to the inventive concept, the first pitch is less than a wavelength of a radiation beam configured to measure the focal variation.

In some embodiments according to the inventive concept, the plurality of diffraction patterns can include a first plurality of diffraction patterns each having a first width, and the substrate can further include a micro-Diffraction Based Overlay (DBO) key on the substrate, the micro-DBO key including a plurality of second diffraction patterns each having a second width that is greater than the first width.

In some embodiments according to the inventive concept, the micro-DBO key can be configured to indicate an overlay error associated with formation of the feature pattern responsive to the radiation beam. In some embodiments according to the inventive concept, the SWG key is surrounded by separate ones of the plurality of second diffraction patterns included in the micro-DBO key.

In some embodiments according to the inventive concept, the in-situ metrology pattern can be configured to produce a phase difference between a transverse electric (TE) polarized radiation component and a transverse magnetic (TM) polarized radiation component included in diffracted radiation from the in-situ metrology pattern. In some embodiments according to the inventive concept, the phase difference indicates a measured height of the in-situ metrology pattern relative to the substrate.

BRIEF DESCRIPTION OF THE DRAWINGS

Exemplary embodiments of the inventive concept will be more clearly understood from the following detailed description taken in conjunction with the accompanying drawings in which.

DETAILED DESCRIPTION OF EMBODIMENTS

Figure 1A:
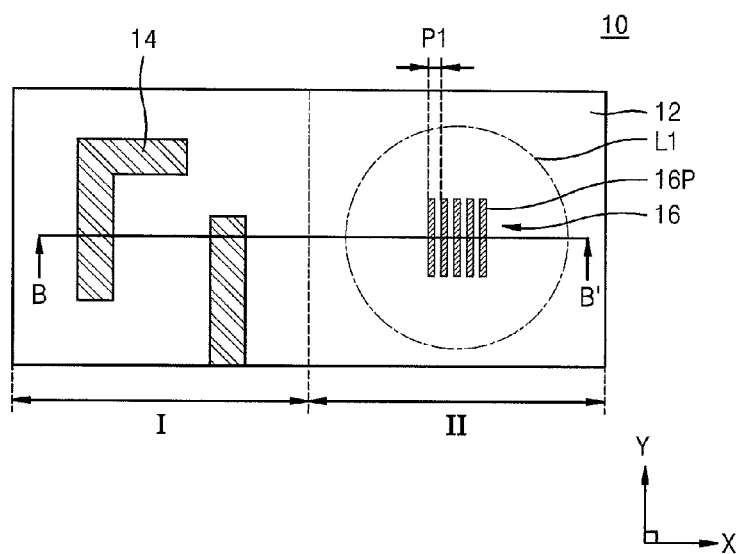
FIG. 1A is a plan view of a substrate target for lithography metrology according to some embodiments of the inventive concept.

As used herein, the term "and/or" includes any and all combinations of one or more of the associated listed items. Expressions such as "at least one of," when preceding a list of elements, modify the entire list of elements and do not modify the individual elements of the list.

Hereinafter, the inventive concept will be described more fully with reference to the accompanying drawings, in which exemplary embodiments of the inventive concept are shown. Like reference numerals in the drawings denote like elements.

The inventive concept may, however, be embodied in many different forms and should not be construed as being limited to the embodiments set forth herein; rather, these embodiments are provided so that this disclosure will be thorough and complete, and will fully convey the inventive concept to one of ordinary skill in the art.

It will be understood that, although the terms first, second, third, etc., may be used herein to describe various elements, regions, layers, sections, and/or components, these elements, components, regions, layers and/or sections should not be limited by these terms. These terms are only used to distinguish one element, component, region, layer or section from another element, component, region, layer or section. Thus, a first element, component, region, layer or section discussed below could be termed a second element, component, region, layer or section without departing from the teachings of the inventive concept. For example, a first component discussed below could be termed a second component, and similarly, a second component may be termed a first component without departing from the teachings of this disclosure.

Unless otherwise defined, all terms (including technical and scientific terms) used herein have the same meaning as commonly understood by one of ordinary skill in the art to which this inventive concept belongs. It will be further understood that terms, such as those defined in commonly used dictionaries, should be interpreted as having a meaning that is consistent with their meaning in the context of the relevant art and will not be interpreted in an idealized or overly formal sense unless expressly so defined herein.

The operations of all methods described herein can be performed in any suitable order unless otherwise indicated herein or otherwise clearly contradicted by context. The inventive concept is not limited to the described order of the operations. For example, operations consecutively described herein may be simultaneously performed in practice, or may be executed in the opposite order to the described order.

As such, variations from the shapes of the illustrations as a result, for example, of manufacturing techniques and/or tolerances, are to be expected. Thus, embodiments of the inventive concept should not be construed as being limited to the particular shapes of regions illustrated herein but are to include deviations in shapes that result, for example, from manufacturing.

Throughout the specification, the term "radiation" will be understood to include any of electromagnetic radiation having various wavelengths, such as, ultraviolet (UV) radiation and extreme ultra-violet (EUV) radiation, and the term "beam" will be understood to include a particle beam, such as an ion beam or an electronic beam. Furthermore, the term "lens" will be understood to include any of various types of optical devices, such as a refractive optical device, a reflective optical device, a magnetic optical device, an electromagnetic optical device, and an electrostatic optical device. Throughout the specification, measuring focal variations of an exposure apparatus may include measuring the location of a focus or measuring an influence of the focal variations. The terms "measurement" and "inspection" may be understood to have the same meaning as each other, in some cases. The terms "determination" and "inferring" may be understood to have the same meaning as each other, in some cases.

FIG. 1A is a plan view of a substrate target 10 for lithography metrology according to some embodiments of the inventive concept.

Figure 1B:
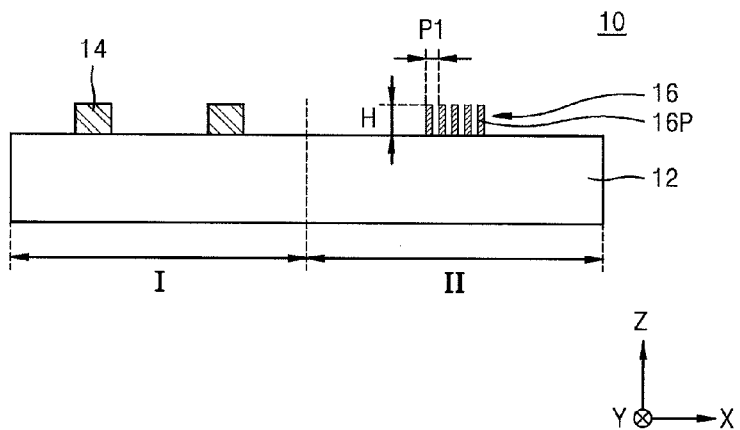
FIG. 1B is a cross-sectional view taken along line B-B' of FIG. 1A.

FIG. 1B is a cross-sectional view taken along line B-B' of FIG. 1A.

Referring to FIGS. 1A and 1B, the substrate target 10 for lithography metrology includes a substrate 12, a plurality of feature patterns 14 formed on a first region I on the substrate 12, and a subwavelength grating (SWG) key 16 formed on a second region II on the substrate 12 to measure a focal variation experienced by (i.e., affecting) the plurality of feature patterns 14 during lithography.

The SWG key 16 may include a plurality of diffraction patterns 16P, which are arranged (i.e., spaced apart on the substrate) at a first pitch P1. The plurality of diffraction patterns 16P and the plurality of feature patterns 14 are formed on the same level relative to a surface of the substrate. The plurality of diffraction patterns 16P may have linear planar structures that are parallel to each other.

The plurality of diffraction patterns 16P of the SWG key 16 and the plurality of feature patterns 14 may be formed of the same material. In some embodiments, the plurality of feature patterns 14 and the plurality of diffraction patterns 16P may be resist patterns.

Figure 5:
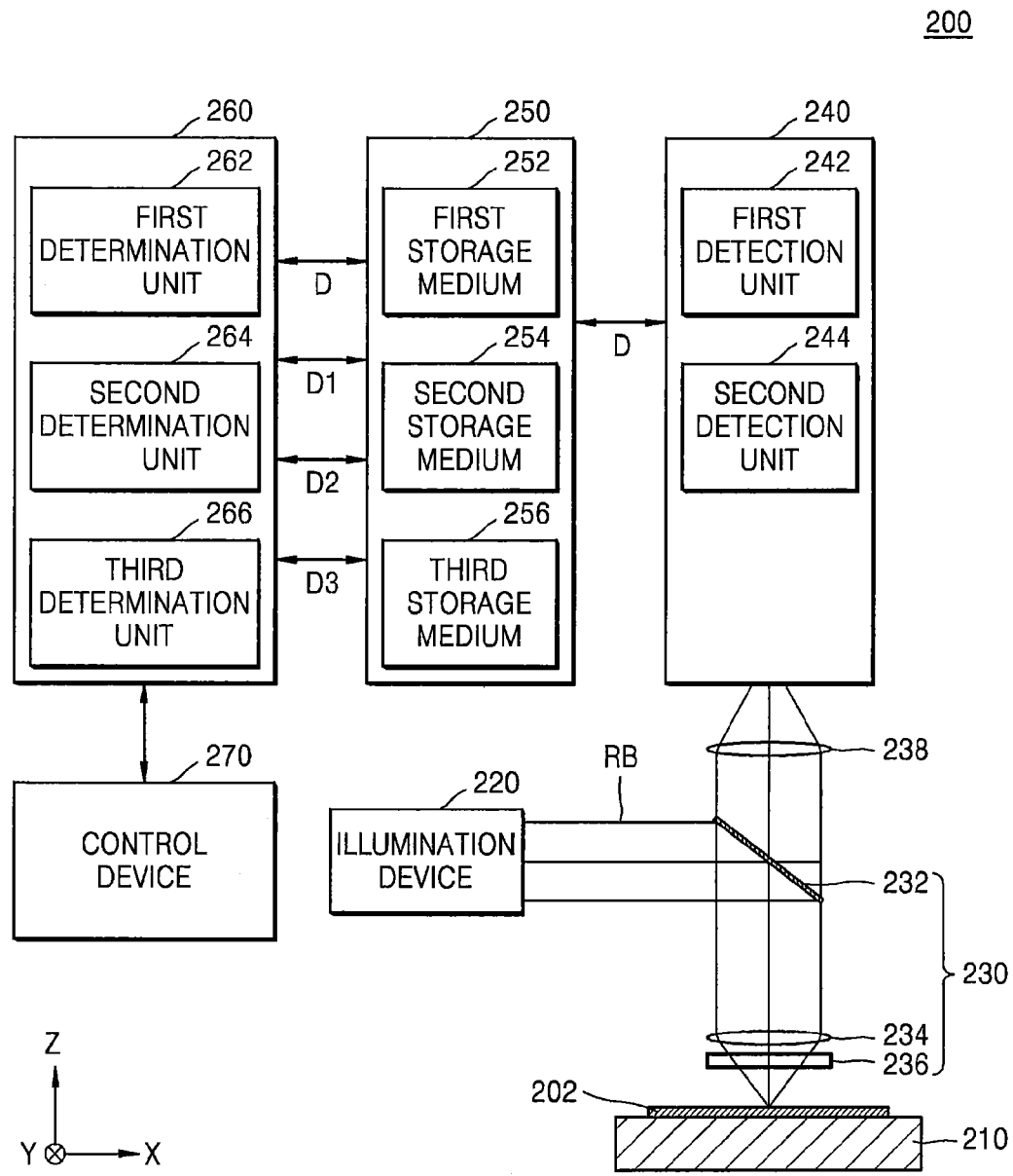
FIG. 5 is a block diagram of a lithography metrology apparatus according to embodiments of the inventive concept.

The first pitch P1 of the plurality of diffraction patterns 16P may be less than a wavelength of a radiation beam that is generated by a lithography metrology apparatus for measuring focal variations of the plurality of feature patterns 14, for example, a lithography metrology apparatus 200 illustrated in FIG. 5. For example, the first pitch P1 of the plurality of diffraction patterns 16P may be less than ½ the wavelength of the radiation beam, but the embodiments of the inventive concept are not limited thereto.

On the second region II of the substrate 12, the plurality of diffraction patterns 16P of the SWG key 16 are formed within a one-time measurement spot L1 formed by one shot of a radiation beam generated by the lithography metrology apparatus for measuring the focal variations of the plurality of feature patterns 14.

Although the SWG key 16 including five diffraction patterns 16P is illustrated in FIGS. 1A and 1B, this is only an example, and the substrate target 10 for lithography metrology may include a SWG key including any of various numbers of diffraction patterns within the scope of the inventive concept.

The first region I on which the plurality of feature patterns 14 are formed may correspond to a pattern region on which patterns used to form some unit devices of an IC device are formed. The second region II on which the SWG key 16 is formed may correspond to a portion of the pattern region on which the plurality of feature patterns 14 are not disposed (i.e., a separate region). Alternatively, the SWG key 16 may be formed on a scribe lane region on the substrate 12.

FIG. 1B illustrates a case where each of the plurality of diffraction patterns 16P constituting the SWG key 16 has a rectangular cross-sectional shape. However, substrate targets according to embodiments of the inventive concept are not limited to the rectangular cross-sectional shape of each of the plurality of diffraction patterns 16P illustrated in FIG. 1B, and they may include a plurality of diffraction patterns each having any of various cross-sectional shapes, for example, a trapezoidal cross-sectional shape or a triangular cross-sectional shape.

Figure 2:
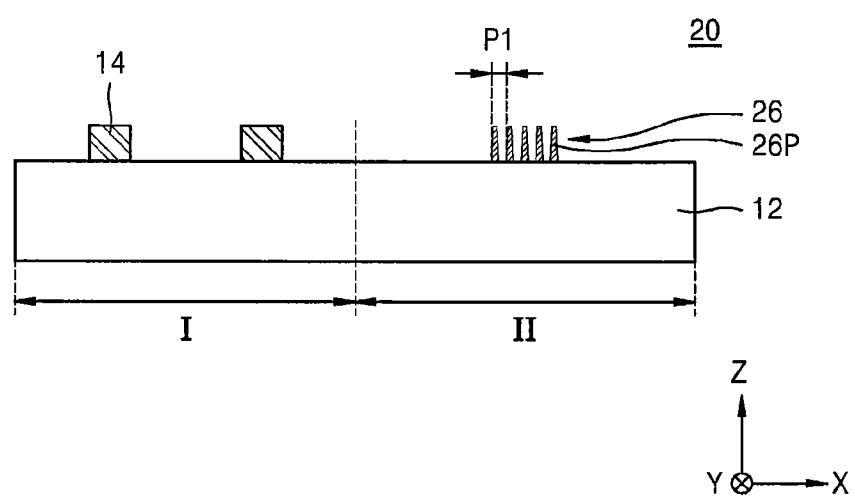
FIG. 2 is a cross-sectional view of a substrate target for lithography metrology according to some embodiments of the inventive concept.

FIG. 2 is a plan view of a substrate target 20 for lithography metrology according to some embodiments of the inventive concept.

The substrate target 20 is the same as or similar to the substrate target 10 of FIGS. 1A and 1B except that an SWG key 26 includes a plurality of diffraction patterns 26P each having a sidewall inclined with respect to a direction (Z direction in FIG. 2) perpendicular to a main surface of the substrate 12.

Figure 3:
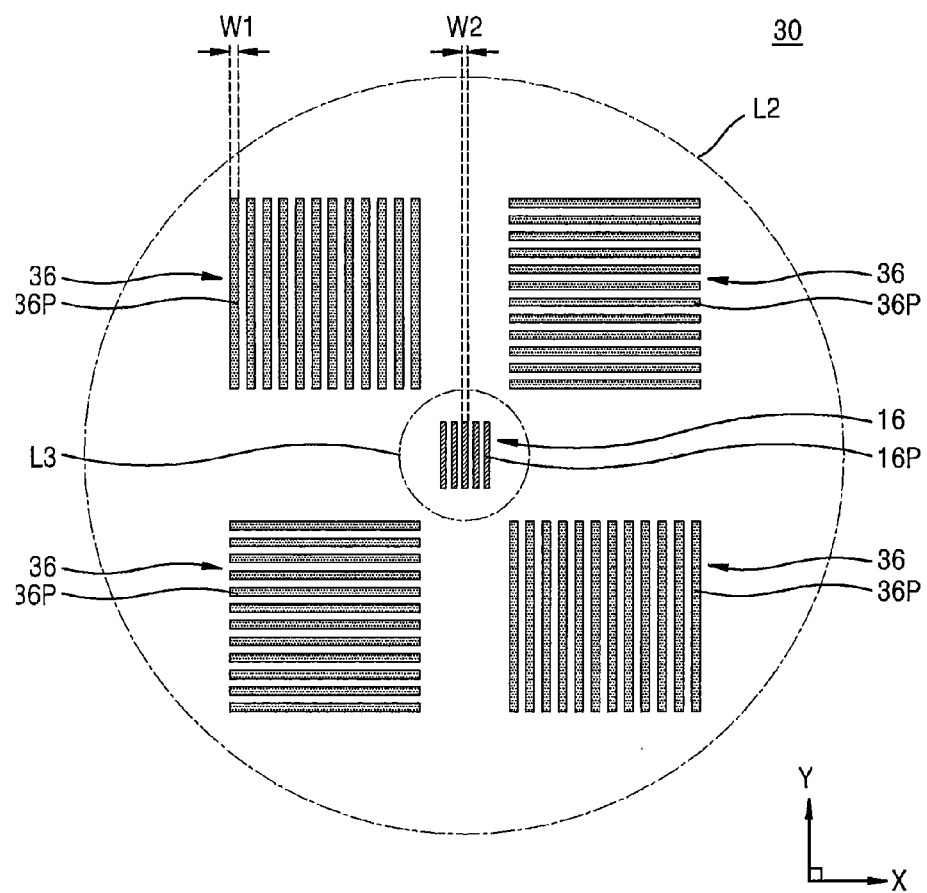
FIG. 3 is a plan view of a substrate target for lithography metrology according to some embodiments of the inventive concept.

FIG. 3 is a plan view of a substrate target 30 for lithography metrology according to some embodiments of the inventive concept.

Similar to the substrate target 10 for lithography metrology of FIGS. 1A and 1B, the substrate target 30 for lithography metrology of FIG. 3 includes the SWG key 16.

The substrate target 30 also includes a plurality of micro diffraction based overlay (DBO) keys 36 formed on the second region II on the substrate 12 (see FIG. 1A). Each of the micro-DBO keys 36 includes a plurality of diffraction patterns 36P. The plurality of diffraction patterns 36P may be linear resist patterns that are parallel to each other. As shown, the different diffraction patterns 36P in each of the keys 36 can be oriented differently.

Each of the plurality of diffraction patterns 36P included in the respective micro-DBO keys 36 has a first width W1 as a minimum width thereof, and each of the plurality of diffraction patterns 16P included in the SWG key 16 has, as a minimum width thereof, a second width W2 that is less than the first width W1.

The micro-DBO keys 36 are formed on the second region II on the substrate 12 (see FIGS. 1A and 1B), within a one-time measurement spot L2 formed by one shot of a radiation beam that is generated by the lithography metrology apparatus for measuring focal variations of the plurality of feature patterns 14 (see FIGS. 1A and 1B), for example, the lithography metrology apparatus 200 illustrated in FIG. 5.

As illustrated in FIG. 3, the SWG key 16 may be formed within an area L3, outside of which is surrounded by the plurality of diffraction patterns 36P, within the one-time measurement spot L2. However, embodiments of the inventive concept are not limited to the example of FIG. 3. For example, the SWG key 16 may be formed on a region spaced apart from the region on which the micro-DBO key 36 is formed.

The SWG key 16 may be used as a key for measuring the focal variations of the plurality of feature patterns 14 (see FIGS. 1A and 1B) formed on the substrate 12. The micro-DBO keys 36 may be used for measuring an overlay error of the plurality of feature patterns 14 (see FIGS. 1A and 1B) formed on the substrate 12.

Figure 4:
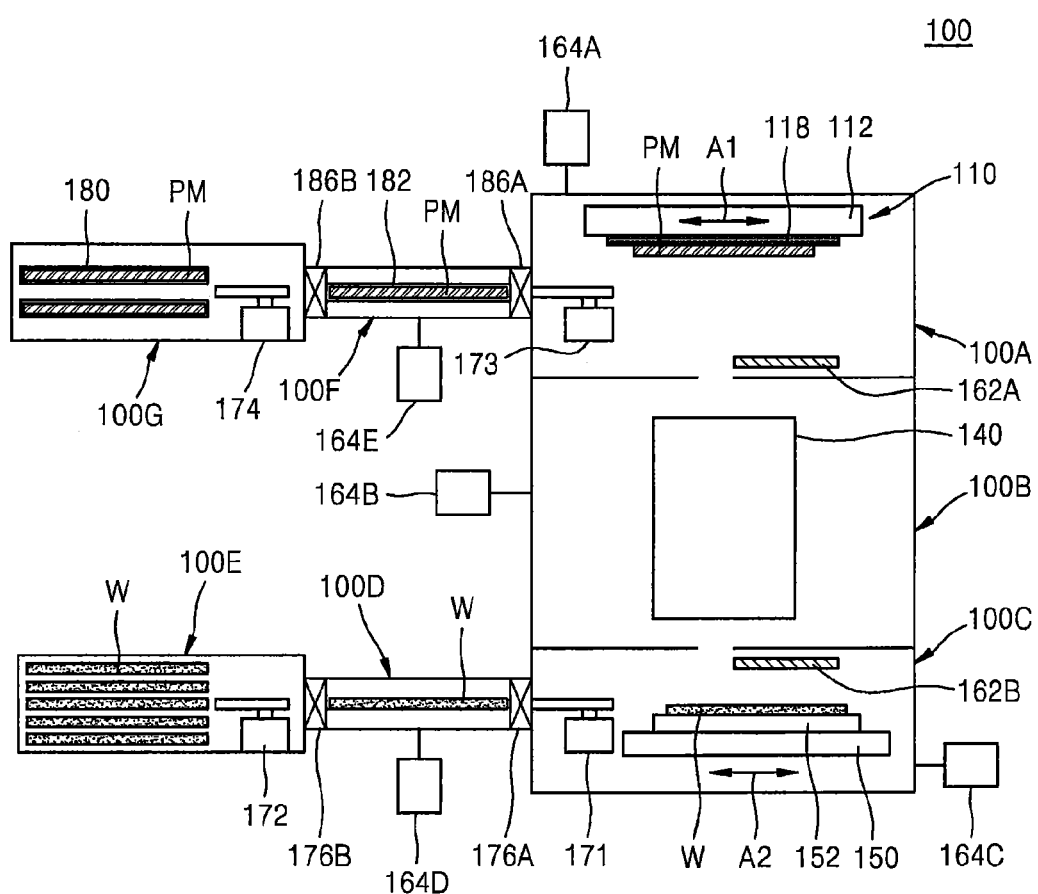
FIG. 4 is a schematic diagram of an exposure apparatus which may be used to manufacture a substrate target for lithography metrology according to embodiments of the inventive concept.

FIG. 4 is a cross-sectional view of an exposure apparatus 100 which may be used to manufacture the substrate targets 10, 20, and 30 for lithography metrology according to some embodiments of the inventive concept illustrated in FIGS. 1A-3.

The exposure apparatus 100 illustrated in FIG. 4 is an exposure apparatus in which a projection optical system can reduces an image of a pattern drawn on a photomask (or also called a reticle) using extreme ultraviolet (EUV) light and can transfer a reduced image to a wafer in a vacuum. However, the substrate targets 10, 20, and 30 for lithography metrology may be formed by using an exposure apparatus having a different structure from the exposure apparatus 100.

Referring to FIG. 4, the exposure apparatus 100 includes a mask stage area 100A, a projection optical system area 100B, and a wafer stage area 100C.

A mask stage 110 in the mask stage area 100A includes a mask stage support 112, and a mask holder system 118 fixed to the mask stage support 112. A photomask PM may be fixed to the mask holder system 118 using an electrostatic chuck.

The mask stage 110 may move the photomask PM in a scan direction indicated by an arrow A1.

In the projection optical system area 100B, a projection optical system 140 may be located for transferring a pattern formed on the photomask PM to a wafer W in the wafer stage area 100C. The wafer W may be fixed onto a wafer chuck 152 on a wafer stage 150. The wafer chuck 152 may move the wafer W in a scan direction indicated by an arrow A2.

The mask stage area 100A including the mask stage 110, the projection optical system area 100B including the projection optical system 140, and the wafer stage area 100C including the wafer stage 150 may be separated from one another by gate valves 162A and 162B. Vacuum exhaust devices 164A, 164B, and 164C may be connected to the mask stage area 100A, the projection optical system area 100B, and the wafer stage area 100C, respectively, to independently control pressures of the mask stage area 100A, the projection optical system area 100B, and the wafer stage area 100C.

A transfer hand 171 is provided to carry the wafer W between (in/out of) the wafer stage area 100C and a loadlock chamber 100D. A vacuum exhaust device 164D is connected to the loadlock chamber 100D. The wafer W may be temporarily stored under air pressure, in a wafer load port 100E. A transfer hand 172 is provided to carry the wafer W between the loadlock chamber 100D and the wafer load port 100E. A gate valve 176A is interposed between the wafer stage area 100C and the loadlock chamber 100D. A gate valve 176B is interposed between the loadlock chamber 100D and the wafer load port 100E.

A transfer hand 173 is provided to carry the photomask PM between the mask stage 110 of the mask stage area 100A and a mask loadlock chamber 100F. A vacuum exhaust device 164E is connected to the mask loadlock chamber 100F. The photomask PM may be temporarily stored under air pressure, in a mask load port 100G. A transfer hand 174 is provided to carry the photomask W between the mask loadlock chamber 100F and the mask load port 100G. A gate valve 186A is interposed between the mask stage area 100A and the mask loadlock chamber 100F. A gate valve 186B is interposed between the mask loadlock chamber 100F and the mask load port 100G.

The photomask PM may be carried from the outside to the exposure apparatus 100 by being accommodated within the photomask carrier 180, and may be carried to the mask load port 100G by being accommodated within the photomask carrier 180.

FIG. 5 is a schematic diagram showing a lithography metrology apparatus 200 according to some embodiments of the inventive concept.

Referring to FIG. 5, the lithography metrology apparatus 200 inspects process parameters that are applied during an exposure process, or process errors such as focal variations and overlay errors, in a non-destructive manner. The lithographic process measuring apparatus 200 is a diffraction-based in-line metrology device (sometimes referred to as carrying over a scatterometer function) which transmits a radiation beam towards the surface of a target substrate, such as, a wafer used to manufacture an IC device, and measures in real time some of the characteristics of a beam diffracted or reflected by the surface of the substrate.

The lithographic process measuring apparatus 200 includes a stage 210 configured to support a target substrate 202 (i.e., a target), an illumination device 220 configured to generate a radiation beam RB, a projection device 230 for projecting the radiation beam RB onto the target substrate 202, and a detection device 240 for detecting some of the characteristics of a beam reflected or diffracted by the target substrate 202.

The target substrate 202 may be any one of the substrate targets 10, 20, and 30 for lithography metrology illustrated in FIGS. 1A-3.

The radiation beam RB is incident upon the target substrate 202 via the projection device 230, which includes a beam splitter 232, an objective lens 234, and a polarizer 236. The polarizer 236 may be configured to polarize the radiation beam RB so that the radiation beam RB may be incident upon the SWG key 16 and/or the micro-DBO key 36 (see FIGS. 1A-3) formed on the target substrate 202.

The illumination device 220 may generate a radiation beam having a wavelength that is greater than the first pitches P1 of the plurality of diffraction patterns 16P and 26P formed on the substrate targets 10, 20, and 30 for lithography metrology illustrated in FIGS. 1A-3. For example, the illumination device 220 may generate a radiation beam having a wavelength that is equal to or greater than twice each of the first pitches P1 of the plurality of diffraction patterns 16P and 26P, but embodiments of the inventive concept are not limited thereto. For example, the illumination device 220 may generate a radiation beam having a wavelength of about 230 to about 850 nm.

The projection device 230 may project the radiation beam so that the radiation beam may be incident upon the target substrate 202 within an angle range of 0° to a Brewster angle with respect to a direction (Z direction of FIG. 5) perpendicular to a direction (X or Y direction of FIG. 5) in which the target substrate 202 extends, for example, within a range of about ±89°.

In some embodiments, the projection device 230 may be configured to project light generated by the illumination device 220 and polarized by the polarizer 236 towards the target substrate 202 when stationary. For example, the projection device 230 may project at least two types of radiation beams as the radiation beam RB. The at least two types of radiation beams may include two types of radiation beams having different wavelengths that are simultaneously incident upon an identical location on the target substrate 202. In another example, the at least two types of radiation beams may include two types of radiation beams that are sequentially incident upon an identical location on the target substrate 202. The two types of radiation beams that are sequentially incident may have identical wavelengths or different wavelengths. For example, the wavelengths of the at least two types of radiation beams may be selected from a wavelength range of about 230 to about 850 nm.

An output beam emitted by the target substrate 202 may be transmitted to the detection device 240 via the beam splitter 232 and a relay lens 238.

The detection device 240 includes a first detection unit 242 configured to detect data D about a transverse electric (TE) polarized light component and a transverse magnetic (TM) polarized light component from, for example, a zero-order diffracted light beam which is an output beam diffracted by the SWG key 16 formed on the target substrate 202. In some embodiments, the data D about the TE polarized light component and the TM polarized light component may indicate about a phase difference between the TE polarized light component and the TM polarized light component.

The lithography metrology apparatus 200 also includes a data storage device 250 which stores the data D about the TE polarized light component and the TM polarized light component detected by the first detection unit 242. The data storage device 250 includes a first storage medium 252 configured to store first data D1 about defocus (that is experimentally determined during an exposure process) based on the data D.

The data D and the first data D1 about the defocus, which are stored in the data storage device 250, may be transmitted to the determination device 260. The determination device 260 includes a first determination unit 262 which infers focal variations experienced by the plurality of feature patterns from the data D and/or the first data D1.

The lithography metrology apparatus 200 may further include a control device 270 which calculates compensated focus data based on the focal variations inferred by the determination device 260.

The data storage device 250 may further include a second storage medium 254 configured to store second data D2 including a depth of focus (DOF), which is the tolerance of defocus that is determined to have been experienced by the target substrate 202 during an exposure process.

The determination device 260 may further include a second determination unit 264. The second determination unit 264 determines whether the defocus that is determined to have been experienced by the target substrate 202 during an exposure process is within a preset DOF range, and can transmit a rework command for the target substrate 202 to the control device 270 when the defocus deviates from the preset DOF range.

When the substrate target 30 for lithography metrology including the SWG key 16 and the micro-DBO key 36 illustrated in FIG. 3 is used as the target substrate 202, the detection device 240 may further include a second detection unit 244 configured to detect data D3 about ±n-order diffracted light beams (where n is an integer equal to or greater than 1) diffracted at an identical angle so as to be symmetrical with each other about a zero-order diffracted light beam from among output beams diffracted by the micro-DBO key 36.

The determination device 260 may further include a third determination unit 266 which infers an overlay error of a plurality of feature patterns, for example, the plurality of feature patterns 14 of FIGS. 1A and 1B, from the data about the ±n-order diffracted light beams detected by the second detection unit 244. In some embodiments, the data D3 can be stored in a third storage medium 256 In some embodiments, the second determination unit 264 may infer the overlay error of the plurality of feature patterns 14 from data D3 about ±1-order diffracted light beams that have been detected by the second detection unit 244. In some embodiments, the second determination unit 264 may infer the overlay error of the plurality of feature patterns 14 from an intensity deviation between the ±1-order diffracted light beams that have been detected by the second detection unit 244.

Figure 6:
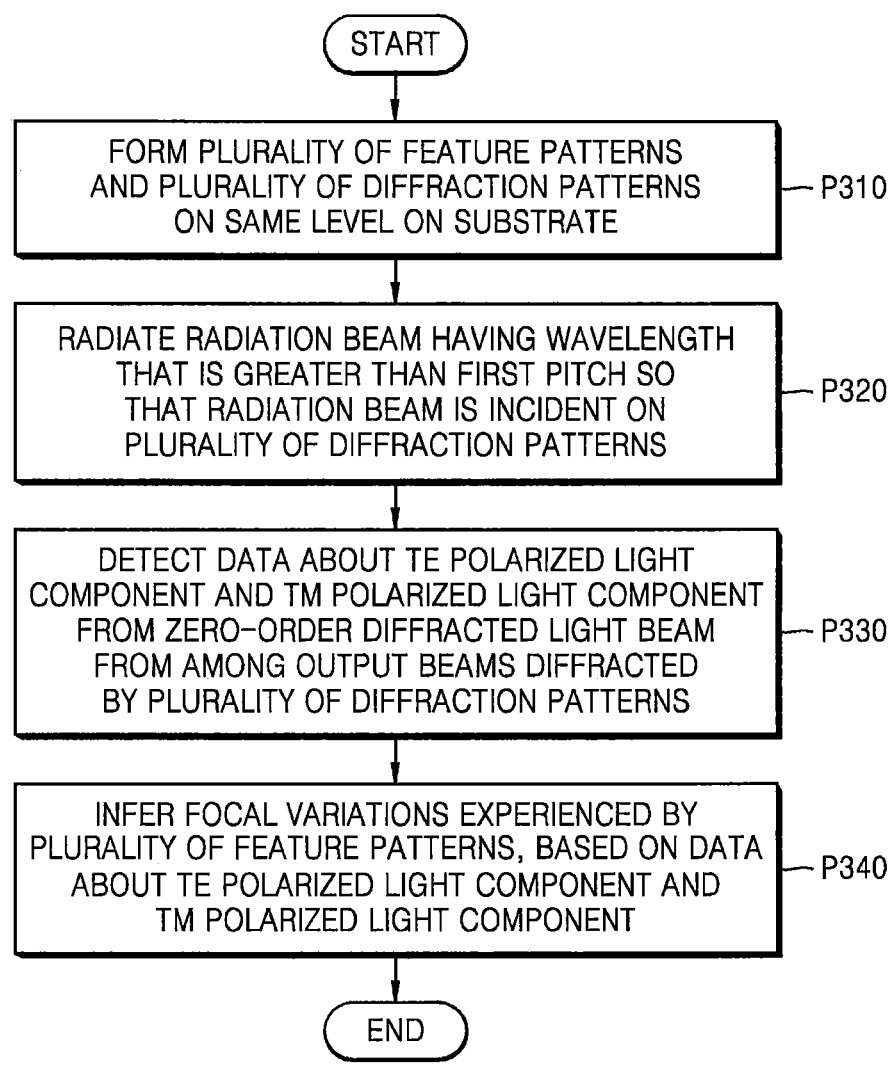
FIG. 6 is a flowchart of a lithography metrology method according to embodiments of the inventive concept.

FIG. 6 is a flowchart of a lithography metrology method according to some embodiments of the inventive concept. The lithography metrology method of FIG. 6 may be performed using the exposure apparatus 100 of FIG. 4 and the lithography metrology apparatus 200 of FIG. 5, but embodiments of the inventive concept are not limited thereto. The lithography metrology method of FIG. 6 may be performed using any of various exposure apparatuses and any of various lithography metrology apparatuses.

Referring to FIG. 6, in operation P310, a plurality of diffraction patterns arranged at intervals of a first pitch and a plurality of feature patterns are formed on the same level on a substrate via lithography.

In some embodiments, the operation P310, the substrate target 10, 20, or 30 for lithography metrology illustrated in FIGS. 1A-3 may be formed. In more detail, to form the substrate target 10 for lithography metrology illustrated in FIGS. 1A and 1B, a photoresist layer is formed on the substrate 12, an exposure process is performed on the photoresist layer by using the exposure apparatus 100 of FIG. 4, and an exposed photoresist layer is then developed, thereby forming the plurality of feature patterns 14 on the first region I of the substrate 12 and forming the SWG key 16 including the plurality of diffraction patterns 16P on the second region II of the substrate 12. The plurality of feature patterns 14 and the diffraction patterns 16P may be photoresist patterns corresponding to a portion of the photoresist layer that is left on the substrate 12 after the photoresist layer is developed.

The plurality of diffraction patterns 16P may be formed to have a pitch, namely, a period, less than the wavelength of a radiation beam that is incident on the plurality of diffraction patterns 16P according to subsequent operation P320, for example, less than half the wavelength of the radiation beam. Thus, the plurality of diffraction patterns 16P may be SWGs each of which is a structure that is less than the wavelength of the light that is radiated onto the substrate in operation P320.

Figure 7:
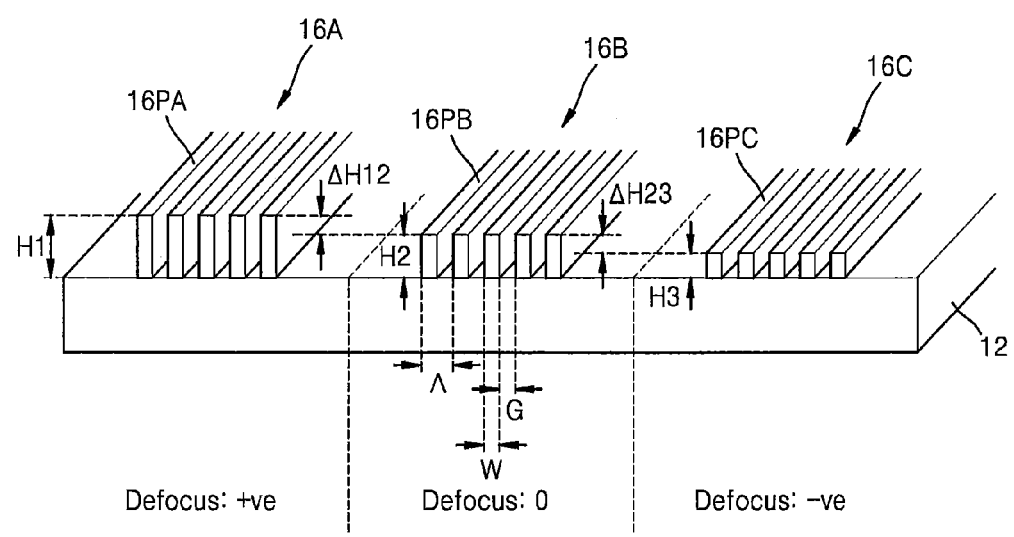
FIG. 7 is a perspective view showing a phenomenon in which a plurality of diffraction patterns respectively included in subwavelength grating (SWG) keys have different heights due to defocus that occurs during lithography, according to embodiments of the inventive concept.

FIG. 7 is a perspective view showing a phenomenon in which a plurality of diffraction patterns 16PA, 16PB, and 16PC respectively included in SWG keys 16A, 16B, and 16C formed on the substrate 12, namely, the plurality of diffraction patterns 16, have different heights H1, H2, and H3 due to defocus that occurs during lithography.

The plurality of diffraction patterns 16PA, 16PB, and 16PC may be set to have identical widths W, and gaps G therebetween may be set to be identical with each other. A lattice period A of the plurality of diffraction patterns 16PA, 16PB, and 16PC of the SWG key 16 is selected by a SWG which is a structure that is less than the wavelength of a radiation beam desired to be used during metrology.

While the plurality of diffraction patterns 16P, constituting the SWG key 16 formed after a developing process, and the plurality of feature patterns 14 are being formed, the plurality of diffraction patterns 16P may have different heights due to focusing performed during lithography, as illustrated in FIG. 7.

Referring back to FIG. 6, in operation P320, a radiation beam having a wavelength that is greater than the first pitch is incident on the plurality of diffraction patterns.

In the case of the substrate target 10 for lithography metrology illustrated in FIGS. 1A and 1B, a radiation beam having a width that is greater than the first pitch P1 of the plurality of diffraction patterns 16P constituting the SWG key 16, for example, a wavelength more than twice the first pitch P1, may be incident.

The incident radiation beam may be light that is polarized within a range from 0° to the Brewster angle with respect to the direction (Z direction in FIG. 5) perpendicular to the direction in which the substrate extends, for example, within a range of about ±89 degrees with respect to the direction perpendicular to the direction in which the substrate extends.

Light radiated to the SWG key 16 is subject to birefringence such that zero-order light diffraction occurs. In the zero-order light diffraction, a phase difference between a TE polarized light component and a TM polarized light component is generated due to the birefringence. The phase difference between the TE polarized light component and the TM polarized light component varies according to the heights of the SWGs of the SWG key 16.

Figure 8:
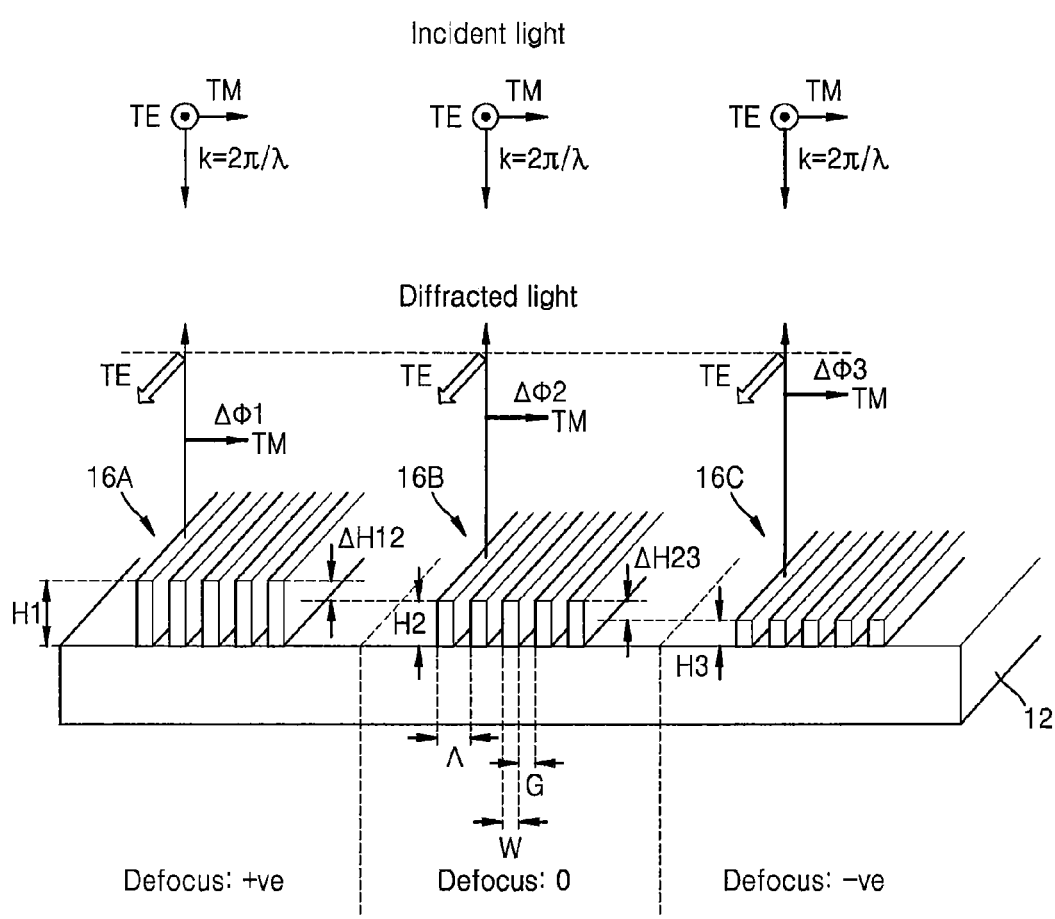
FIG. 8 is a perspective view illustrating phase differences between transverse electric (TE) polarized light components and transverse magnetic (TM) polarized light components due to birefringence in zero-order light diffraction of the light radiated to a SWG key of a substrate target for lithography metrology, according to embodiments of the inventive concept.

FIG. 8 is a perspective view for explaining phase differences $\Delta\varphi1$, $\Delta\varphi2$, and $\Delta\varphi3$ between TE polarized light components and TM polarized light components due to birefringence in zero-order light diffraction of the light radiated to the SWG key 16.

Figure 9:
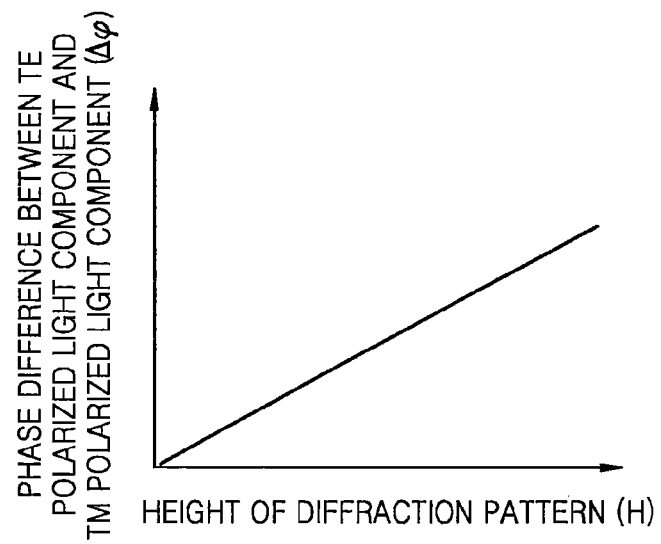
FIG. 9 is a graph showing an exemplary relationship between a phase difference between a TE polarized light component and a TM polarized light component and a height of a plurality of diffraction patterns included in a substrate target for lithography metrology, according to embodiments of the inventive concept.

FIG. 9 is a graph showing an exemplary relationship between a phase difference $\Delta\varphi$ between a TE polarized light component and a TM polarized light component and a height H of the plurality of diffraction patterns 16P.

Referring to FIGS. 8 and 9, a transmittance property of the plurality of diffraction patterns 16P of the SWG key 16 is usually greatly affected by the lattice period A and the height H (see FIG. 1B) of the plurality of diffraction patterns 16P. When polarized light is radiated to the SWG key 16, the polarization state of the light that is diffracted may change, and the amount of the change of the polarization state of the light may be proportional to the heights H1, H2, and H3 of the plurality of diffraction patterns 16PA, 16PB, and 16PC, which are SWGs. Accordingly, as illustrated in FIG. 9, the phase difference $\Delta\varphi$ between the TE polarized light component and the TM polarized light component may linearly increase with the height H of the plurality of diffraction patterns 16P. However, embodiments of the inventive concept are not limited to the variation pattern of the phase difference $\Delta\varphi$ of FIG. 9. For example, the phase difference $\Delta\varphi$ between the TE polarized light component and the TM polarized light component may increase non-linearly with the height H of the plurality of diffraction patterns 16P.

Referring back to FIG. 6, in operation P330, data about a TE polarized light component and a TM polarized light component is detected from a zero-order diffracted light beam from among output beams diffracted by the plurality of diffraction patterns.

The data about the TE polarized light component and the TM polarized light component may include data about the phase difference $\Delta\varphi$ between the TE polarized light component and the TM polarized light component described above with reference to FIGS. 8 and 9.

In some embodiments, the data about the TE polarized light component and the TM polarized light component may be detected by the first detection unit 242 of the detection device 240 of FIG. 5.

In operation P340, focal variations experienced by the plurality of feature patterns during the lithography are inferred based on the data about the TE polarized light component and the TM polarized light component.

In some embodiments, to infer the focal variations experienced by the plurality of feature patterns in operation P340, a graph obtained based on repetitive experiments as illustrated in FIG. 9 or a similar graph thereto may be used. Alternatively, the focal variations experienced by the plurality of feature patterns may be inferred in operation P340, based on an equation in which the relationship between the phase difference $\Delta\varphi$ between the TE polarized light component and the TM polarized light component and the height H of the plurality of diffraction patterns 16P is defined by reflecting various process parameters for lithography. Alternatively, the focal variations experienced by the plurality of feature patterns may be inferred using the values that are set based on experimental values of correlations between the heights H of the plurality of diffraction patterns 16P and defocus aberrations as illustrate n FIGS. 7 and 8.

Figure 10:
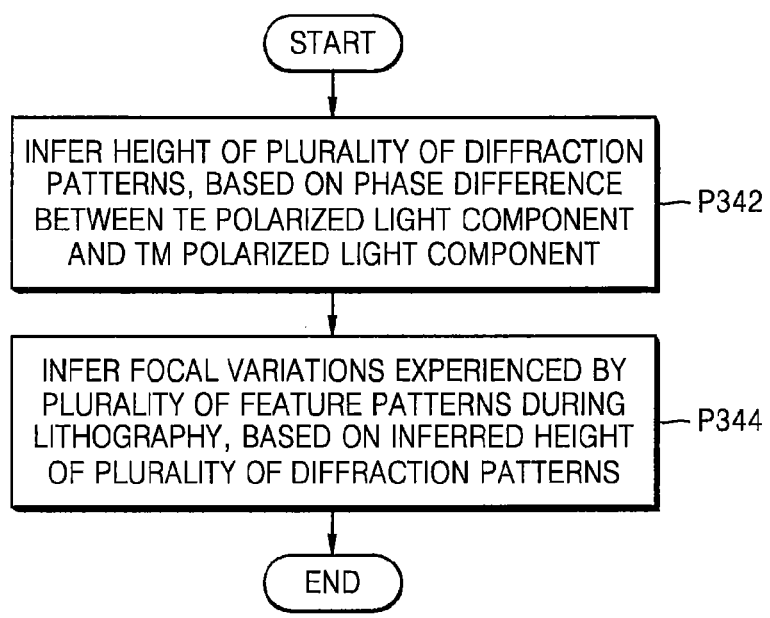
FIG. 10 is a flowchart of an exemplary operation of inferring focal variations applied during lithography and experienced by a plurality of feature patterns, which is included in a lithography metrology method according to embodiments of the inventive concept.

FIG. 10 is a flowchart of an exemplary operation of inferring focal variations applied during lithography and experienced by a plurality of feature patterns, which is included in the lithography metrology method of FIG. 6.

Referring to FIG. 10, first, in operation P342, the height of a plurality of diffraction patterns is inferred based on the phase difference between the TE polarized light component and the TM polarized light component detected in operation P330 of FIG. 6.

In operation P344, the focal variations determined to be experienced by the plurality of feature patterns during lithography are inferred based on the height of the plurality of diffraction patterns inferred in operation P342.

According to the lithography metrology method described with reference to FIGS. 6-10, a phase difference between a TE polarized light component and a TM polarized light component from among a diffracted output beam is analyzed from a plurality of diffraction patterns that have different heights in proportion to focusing of an exposure apparatus, and thus focusing experienced by a target substrate during lithography may be inferred. In this way, minute focal variations during exposure of the target substrate may be measured. For example, even focal variations of thickness of several nm may be measured. Therefore, in-line (or in situ) monitoring of focal variations of an exposure apparatus applied during lithography for manufacturing an integrated circuit (IC) device and fine focal variations experienced during lithography may be possible.

Figure 11:
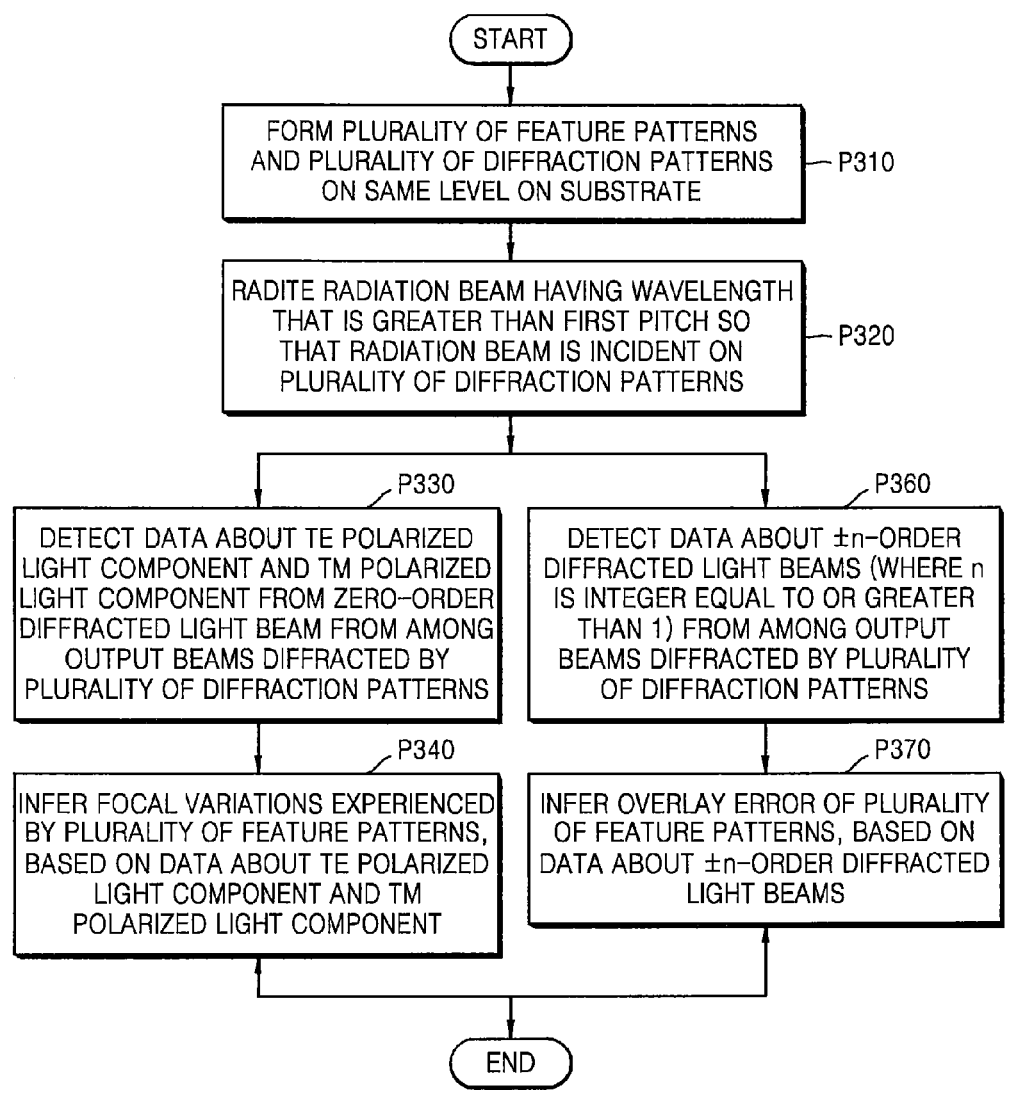
FIG. 11 is a flowchart of an exposure process measuring method according to some embodiments of the inventive concept.

FIG. 11 is a flowchart of a lithography metrology method according to some embodiments of the inventive concept.

The lithography metrology method of FIG. 11 includes some of the operations described above with reference to FIG. 6.

Referring to FIG. 11, operations P310 and P320 described above with reference to FIG. 6 are performed.

In particular, when the plurality of feature patterns and the plurality of diffraction patterns are formed on the substrate in operation P310, the SWG key 16 and the micro-DBO key 36 may also be formed on the second region II of the substrate target 12 as illustrated in FIG. 3.

When the radiation beam having a wavelength that is greater than the first pitch of the plurality of diffraction patterns is incident on the plurality of diffraction patterns in operation P320, the radiation beam may be incident on both the SWG key 16 and the micro-DBO key 36.

Figure 12:
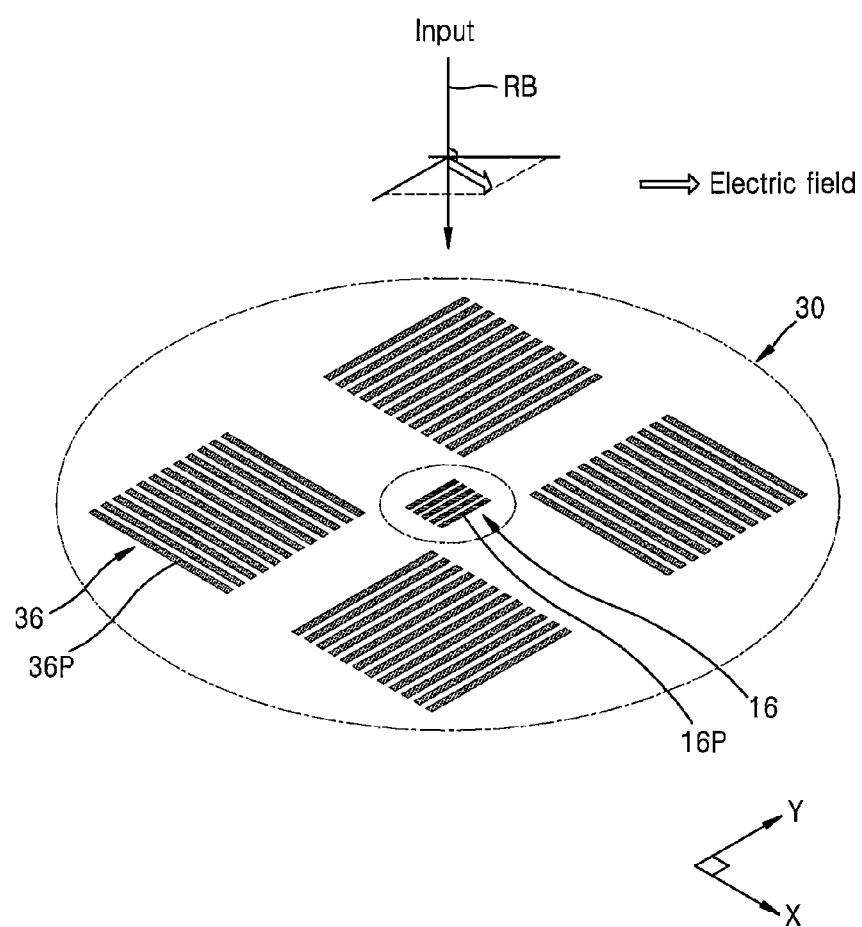
FIG. 12 is a perspective view illustrating a case where a radiation beam having a wavelength that is greater than a pitch of a plurality of diffraction patterns is incident on a substrate target for lithography metrology according to some embodiments of the inventive concept.

FIG. 12 is a perspective view illustrating a case where a radiation beam RB having a wavelength that is greater than the first pitch of the plurality of diffraction patterns 16P is incident on the substrate target 30 of FIG. 3.

In operation P360, data about ±n-order diffracted light beams (where n is an integer equal to or greater than 1) diffracted at identical angles so as to be symmetrical with each other about the zero-order diffracted light beam from among output beams diffracted by the plurality of diffraction patterns is detected.

The data about the ±n-order diffracted light beams may include data about a deviation between the intensities of the ±n-order diffracted light beams.

The ±n-order diffracted light beams detected in operation P360 of FIG. 11 may be selected from, from example, beams that are output by the micro-DBO key 36 of FIG. 3. The zero-order diffracted light beam for detecting the TE polarized light component and the TM polarized light component in operation P330 of FIG. 11 may correspond to the output beams of the SWG key 16 of FIG. 3.

In some embodiments, the data about the ±n-order diffracted light beams may be detected by the second detection unit 244 of the detection device 240 of FIG. 5.

Prior to operation P360, the operation P320 of radiating the radiation beam onto the substrate may include a first incidence operation of radiating a first radiation beam having a wavelength greater than the first pitch of the plurality of diffraction patterns onto the substrate and a second incidence operation of radiating a second radiation beam onto the region of the substrate where the first radiation beam is incident. For example, the wavelength of the second radiation beam may be equal to that of the first radiation beam. In another example, the wavelength of the second radiation beam may be different from that of the first radiation beam.

Figure 13:
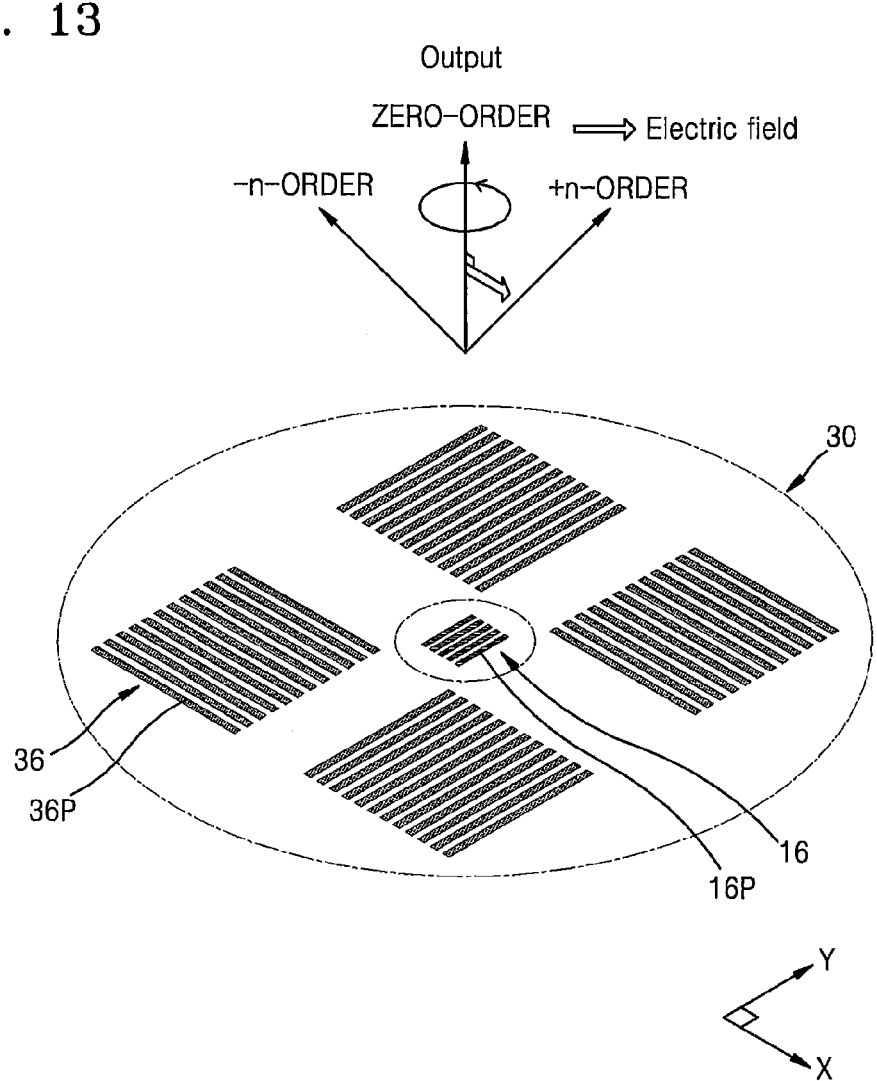
FIG. 13 is a perspective view illustrating diffracted light beams obtained from a radiation beam incident on a substrate target for lithography metrology according to some embodiments of the inventive concept.

FIG. 13 is a perspective view illustrating diffracted light beams obtained from the radiation beam RB incident on the substrate target 30 of FIG. 3.

Referring to FIG. 13, when a radiation beam RB having one type of wavelength as illustrated in FIG. 12 is radiated one time in operation P320 of FIG. 11, a phase difference between a TE polarized light component and a TM polarized light component of the zero-order diffracted light beam output by the SWG key 16 from among diffracted beams obtained from the radiation beam RB may be detected in operation P330. In operation P340, focal variations experienced by the plurality of feature patterns may be inferred based on data about the phase difference between the TE polarized light component and the TM polarized light component of the zero-order diffracted light beam. In operation P360, the intensity deviation between the ±n-order diffracted light beams output by the micro-DBO key 36 from among the diffracted beams are obtained from the radiation beam RB. In operation P370, an overlay error of the plurality of feature patterns may be inferred based on the intensity deviation between the ±n-order diffracted light beams. In some embodiments, the overlay error may be inferred using an intensity deviation between ±1-order diffracted light beams from among the diffracted beams obtained from the radiation beam RB.

Figure 14:
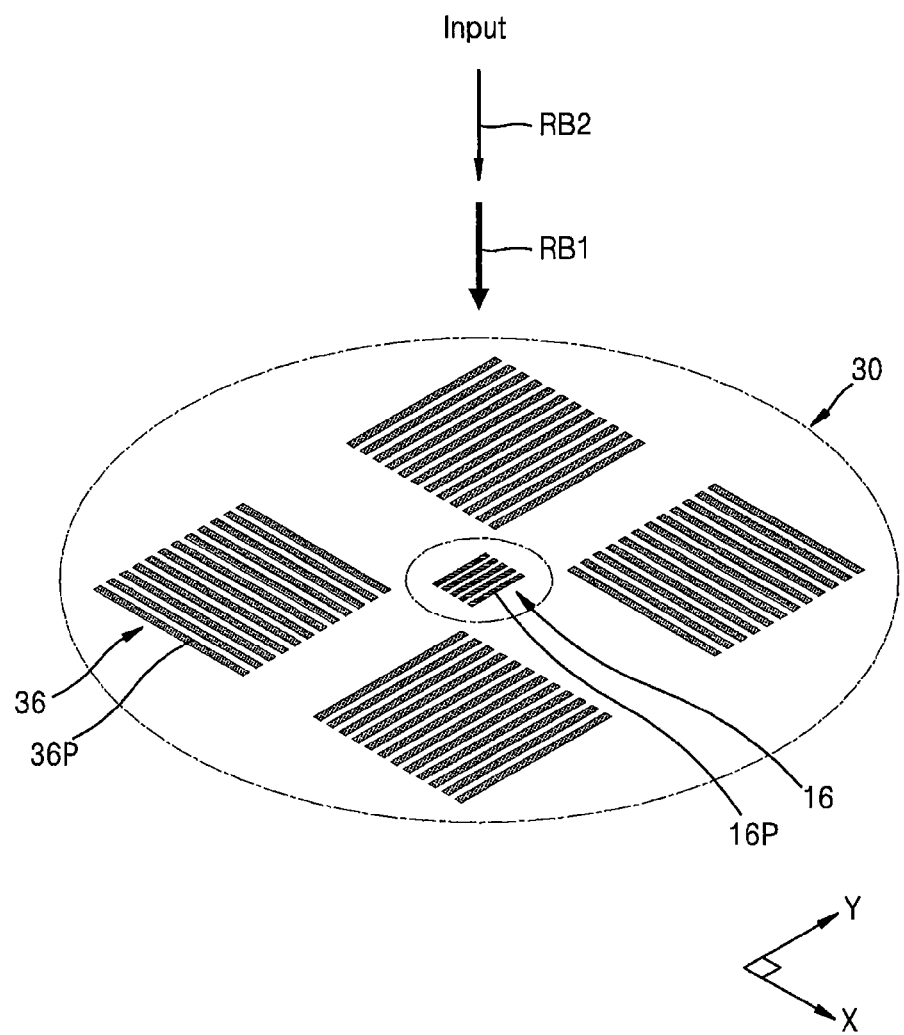
FIG. 14 is a perspective view illustrating a case where a first radiation beam for detecting a phase difference between a TE polarized light component and a TM polarized light component of a zero-order diffracted light beam, and a second radiation beam for detecting an intensity deviation between ±n-order diffracted light beams are incident on a substrate target for lithography metrology according to some embodiments of the inventive concept.

FIG. 14 is a perspective view illustrating a case where a first radiation beam RB1 for detecting the phase difference between the TE polarized light component and the TM polarized light component of the zero-order diffracted light beam, and a second radiation beam RB2 for detecting the intensity deviation between the ±n-order diffracted light beams are simultaneously or sequentially incident on the substrate target 30 of FIG. 3.

In some examples, the first radiation beam RB1 and the second radiation beam RB2 may have identical wavelengths. In other examples, the first radiation beam RB1 and the second radiation beam RB2 may have different wavelengths. The respective wavelengths of the first radiation beam RB1 and the second radiation beam RB2 may be selected from the range of about 230 to about 850 nm.

In some examples, the first radiation beam RB1 and the second radiation beam RB2 may be simultaneously incident on the same location on the substrate target 30. In other examples, the first radiation beam RB1 and the second radiation beam RB2 may be sequentially incident on the same location on the substrate target 30. In this case, the first radiation beam RB1 may be incident prior to the second radiation beam RB2, or the second radiation beam RB2 may be incident prior to the first radiation beam RB1.

In other examples, the first radiation beam RB1 and the second radiation beam RB2 may be incident when the substrate target 30 is stationary.

Figure 15:
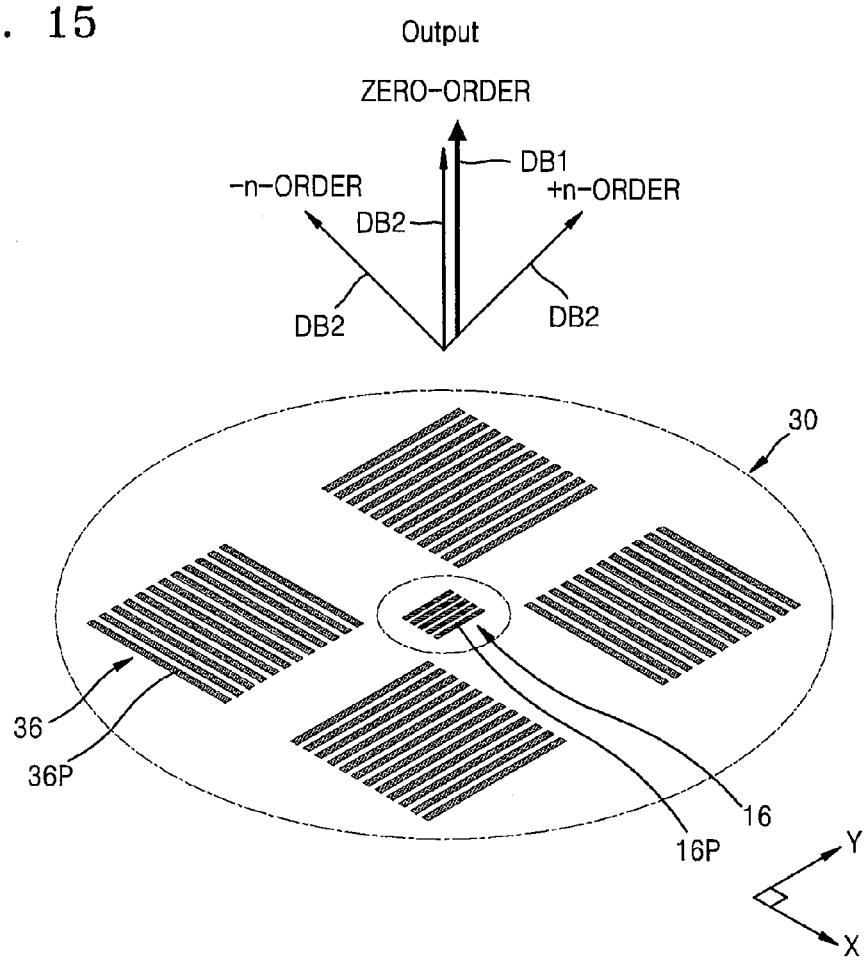
FIG. 15 is a perspective view illustrating diffracted beams obtained from a substrate target for lithography metrology when a first radiation beam for detecting a phase difference between a TE polarized light component and a TM polarized light component of a zero-order diffracted light beam, and a second radiation beam for detecting an intensity deviation between ±n-order diffracted light beams are incident on the substrate target for lithography metrology according to some embodiments of the inventive concept.

FIG. 15 is a perspective view illustrating a case where the first radiation beam RB1 for detecting the phase difference between the TE polarized light component and the TM polarized light component of the zero-order diffracted light beam, and the second radiation beam RB2 for detecting the intensity deviation between the ±n-order diffracted light beams are separately incident on the substrate target 30 of FIG. 3.

Referring to FIG. 15, in operation P330, a phase difference between a TE polarized light component and a TM polarized light component of a zero-order diffracted light beam which is a diffracted light beam DB1 obtained by the SWG key 16 on which the first radiation beam RB1 has been incident is detected. In operation P340, focal variations experienced by the plurality of feature patterns may be inferred based on data about the phase difference between the TE polarized light component and the TM polarized light component of the zero-order diffracted light beam. In operation P360, an intensity deviation between ±n-order diffracted light beams from among diffracted beams DB2 obtained by the micro-DBO key 36 on which the second radiation beam RB2 has been incident. In operation P370, an overlay error of the plurality of feature patterns may be inferred based on the intensity deviation between the ±n-order diffracted light beams. In some embodiments, the overlay error may be inferred using an intensity deviation between ±1-order diffracted light beams from among diffracted beams obtained from the second radiation beam RB2.

Operation P360 of FIG. 11 of detecting the data about the ±n-order diffracted light beams may be performed simultaneously with operation P330 of detecting the data about the TE polarized light component and the TM polarized light component, or operations P360 and P330 may be performed in a certain order. In some embodiments, operation P370 of inferring the overlay error of the plurality of feature patterns may be performed simultaneously with operation P340 of inferring the focal variations experienced by the plurality of feature patterns. In other embodiments, the operation P370 and the operation P340 may be sequentially performed. For example, operation P370 of inferring the overlay error of the plurality of feature patterns may be performed before or after operation P340 of inferring the focal variations experienced by the plurality of feature patterns.

In operation P370, the overlay error of the plurality of feature patterns is inferred from the data about the ±n-order diffracted light beams detected in operation P360.

In some embodiments, the overlay error of the plurality of feature patterns may be inferred using the intensity deviation between the ±n-order diffracted light beams.

According to the lithography metrology method described with reference to FIG. 11, focal variations experienced by a plurality of feature patterns formed on the same level as the a plurality of diffraction patterns may be measured using a zero-order diffracted light beam obtained by a SWG key from among output beams diffracted by the plurality of diffraction patterns, and an overlay error of the plurality of feature patterns may be measured using ±n-order diffracted light beams obtained by a micro-DBO key from among the output beams diffracted by the plurality of diffraction patterns. Accordingly, the focal variations and the overlay error may be simultaneously measured using a single substrate target, leading to a reduction in metrology time. Therefore, the productivity of the method of manufacturing an IC device may improve.

Figure 16:
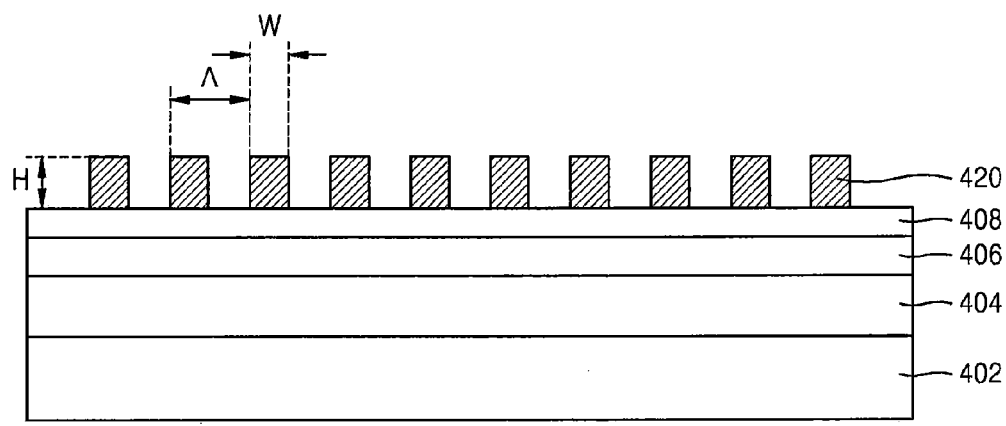
FIG. 16 is a cross-sectional view of a plurality of diffraction patterns formed on a substrate to evaluate the effect of a duty cycle of the plurality of diffraction patterns upon a phase difference between a TE polarized light component and a TM polarized light component obtained from a zero-order diffracted light beam from among output beams diffracted by the plurality of diffraction patterns according to a lithography metrology method according to some embodiments of the inventive concept.

FIG. 16 is a cross-sectional view of a structure of a plurality of diffraction patterns formed on a substrate in order to evaluate an effect of a duty cycle of the plurality of diffraction patterns upon a phase difference between a TE polarized light component and a TM polarized light component obtained from a zero-order diffracted light beam from among output beams diffracted by the plurality of diffraction patterns according to a lithography metrology method according to embodiments of the inventive concept.

Referring to FIG. 16, a sample used to evaluate the effect of the duty cycle upon the phase difference between the TE polarized light component and the TM polarized light component was manufactured as follows.

A hard mask layer 404, an inorganic antireflection layer 406, and an organic antireflection layer 408 were sequentially formed on a silicon substrate 402, a photoresist layer was formed on the organic antireflection layer 408, and a plurality of diffraction patterns 420 including a plurality of lines arranged in parallel were formed to have various periods A, various duty cycles DC, and various heights H, via exposure and development of the photoresist layer. In the present specification, a duty cycle DC is defined as a value obtained by dividing a width W of each of the plurality of diffraction patterns 420 by a period A.

The hard mask layer 404 was formed of a carbon-containing film formed of a spin-on hardmask (SOH) material including an organic compound with a relatively high carbon content of about 85 to about 99% by weight based on the overall weight of the organic compound. The inorganic antireflection layer 406 was formed of SiON. The organic antireflection layer 408 was formed of bottom anti-reflective coating (BARC).

FIGS. 17A-17E are graphs showing an evaluation of the effect of a variation in the height H of each of the plurality of diffraction patterns 420 upon the phase difference between the TE polarized light component and the TM polarized light component of a zero-order diffracted light beam obtained by the plurality of diffraction patterns 420 receiving and diffracting a radiation beam with a wavelength of 633 nm, in the cases of various samples having various periods A, various duty cycles DC, and various heights H in the structure of FIG. 16.

Figure 17A:
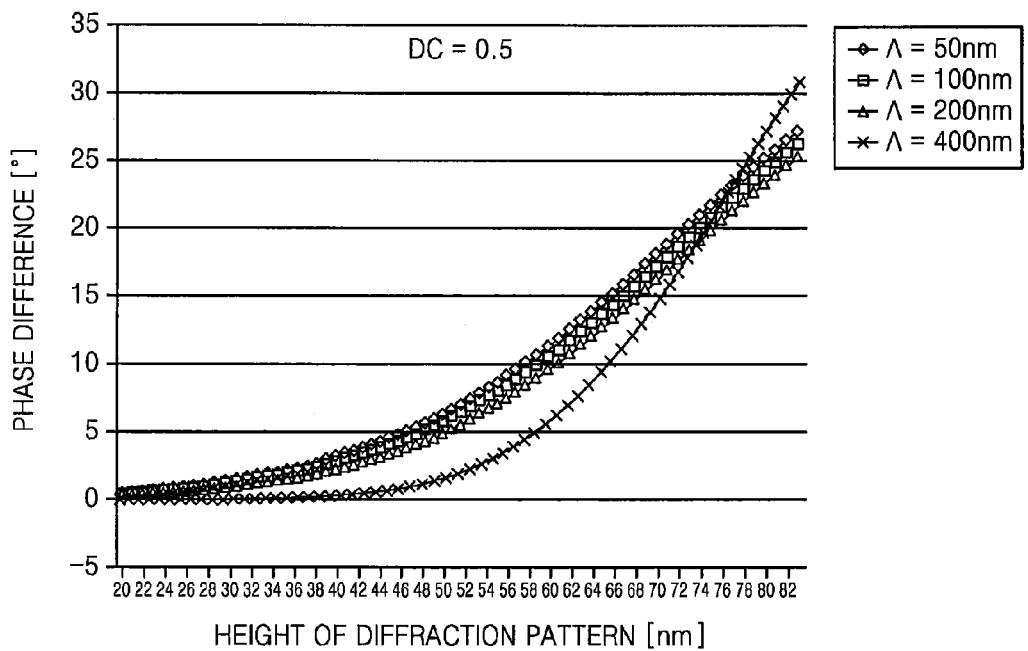
FIGS. 17A-17E are graphs showing phase differences between TE polarized light components and TM polarized light components versus a height of each of a plurality of diffraction patterns of a substrate target for lithography metrology.

In more detail, FIG. 17A is a graph showing a result of detecting a phase difference between a TE polarized light component and a TM polarized light component of a zero-order diffracted light beam according to the height H of the plurality of diffraction patterns 420 when the duty cycle DC of the plurality of diffraction patterns 420 was fixed at 0.5 and the period A thereof was 50 nm, 100 nm, 200 nm, and 400 nm.

Figure 17B:
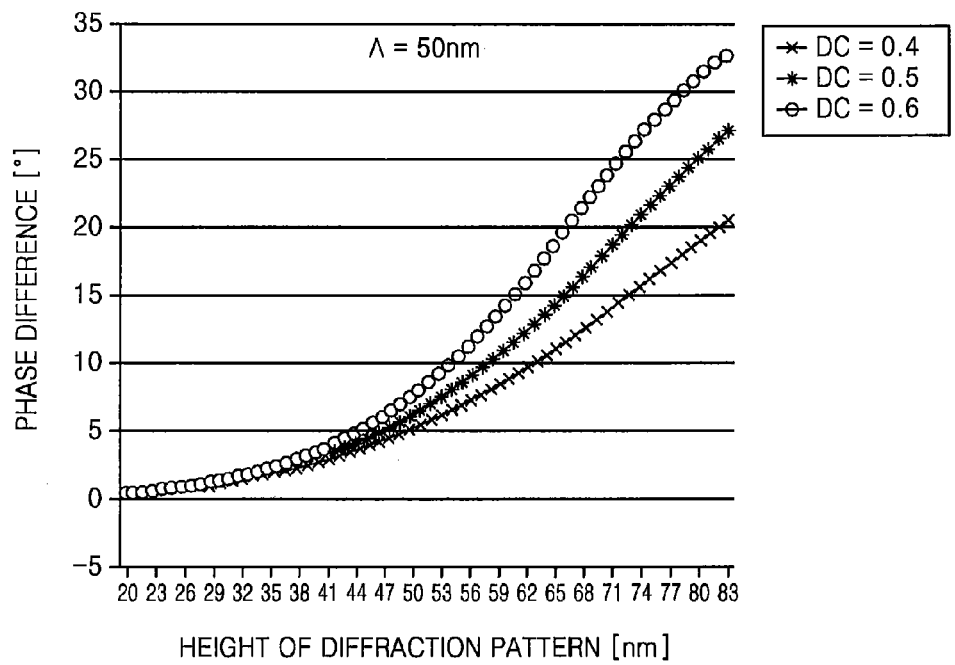

FIG. 17B is a graph showing a result of detecting a phase difference between a TE polarized light component and a TM polarized light component of a zero-order diffracted light beam according to the height H of the plurality of diffraction patterns 420 when the period A of the plurality of diffraction patterns 420 was fixed at 50 nm and the duty cycle DC thereof was 0.4, 0.5, and 0.6.

Figure 17C:
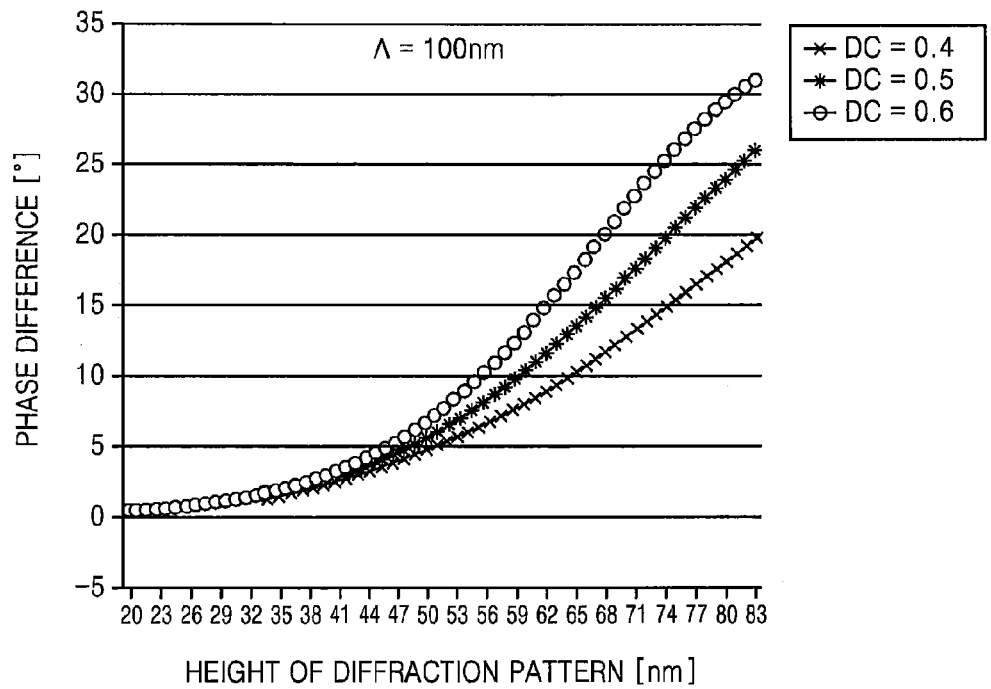

FIG. 17C is a graph showing a result of detecting a phase difference between a TE polarized light component and a TM polarized light component of a zero-order diffracted light beam according to the height H of the plurality of diffraction patterns 420 when the period A of the plurality of diffraction patterns 420 was fixed at 100 nm and the duty cycle DC thereof was 0.4, 0.5, and 0.6.

Figure 17D:
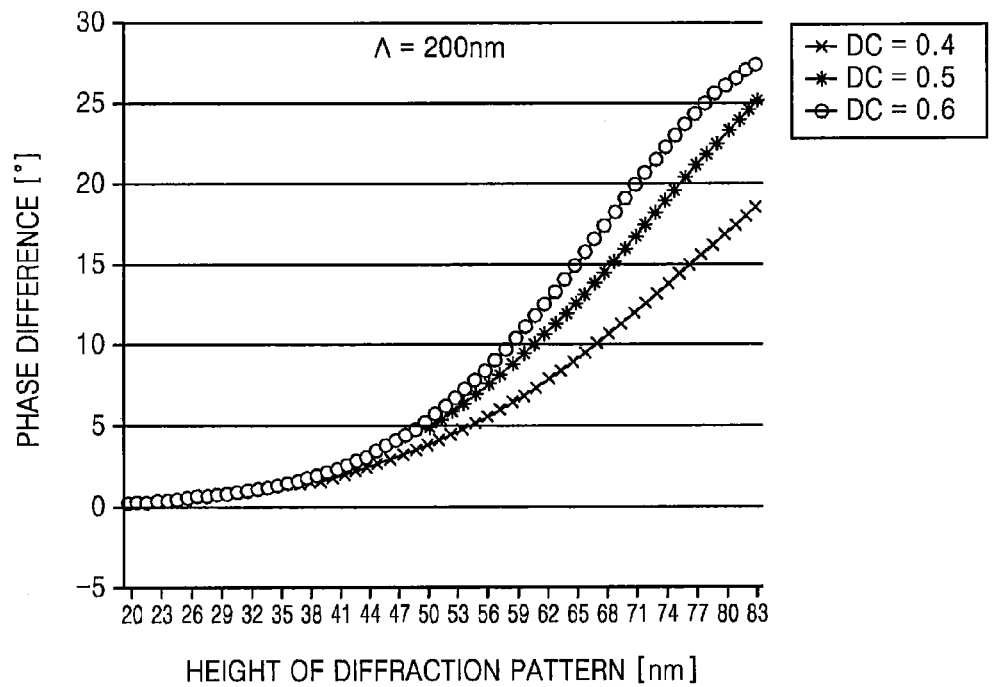

FIG. 17D is a graph showing a result of detecting a phase difference between a TE polarized light component and a TM polarized light component of a zero-order diffracted light beam according to the height H of the plurality of diffraction patterns 420 when the period A of the plurality of diffraction patterns 420 was fixed at 200 nm and the duty cycle DC thereof was 0.4, 0.5, and 0.6.

Figure 17E:
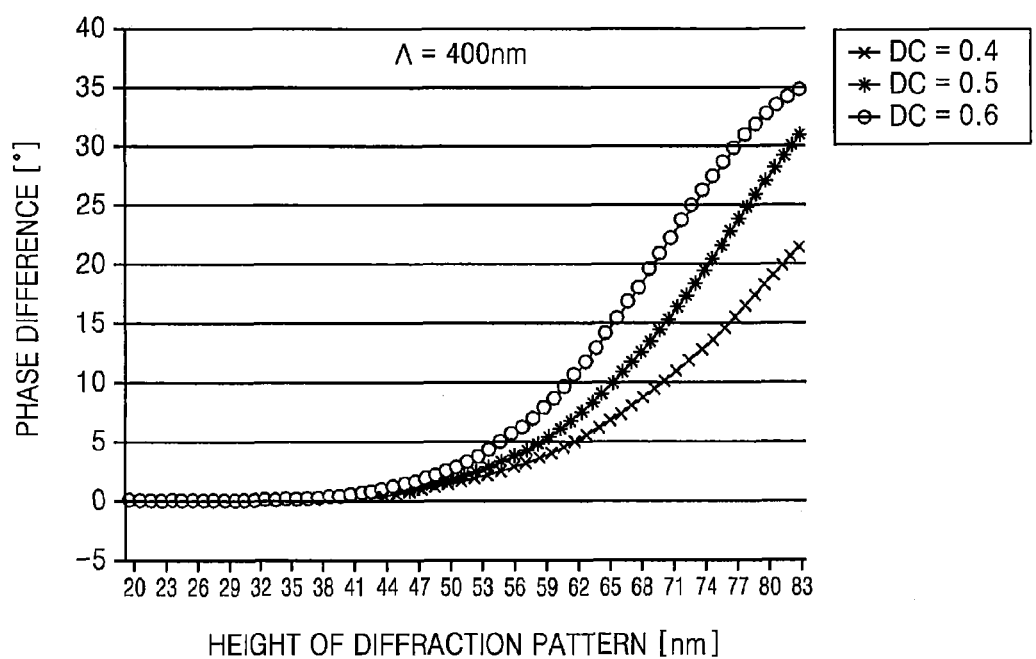

FIG. 17E is a graph showing a result of detecting a phase difference between a TE polarized light component and a TM polarized light component of a zero-order diffracted light beam according to the height H of the plurality of diffraction patterns 420 when the period A of the plurality of diffraction patterns 420 was fixed at 400 nm and the duty cycle DC thereof was 0.4, 0.5, and 0.6.

From the results of FIGS. 17A-17E, it is apparent that, even when the period A and the duty cycle DC of the plurality of diffraction patterns 420 have different conditions, the phase difference between the TE polarized light component and the TM polarized light component increases with an increase in the height H of the plurality of diffraction patterns 420. Accordingly, focal variations experienced by a feature pattern formed simultaneously with the plurality of diffraction patterns 420 may be inferred based on the phase differences between the TE polarized light components and the TM polarized light components measured using the plurality of diffraction patterns 420 having various periods A and various duty cycles DC.

Figure 18:
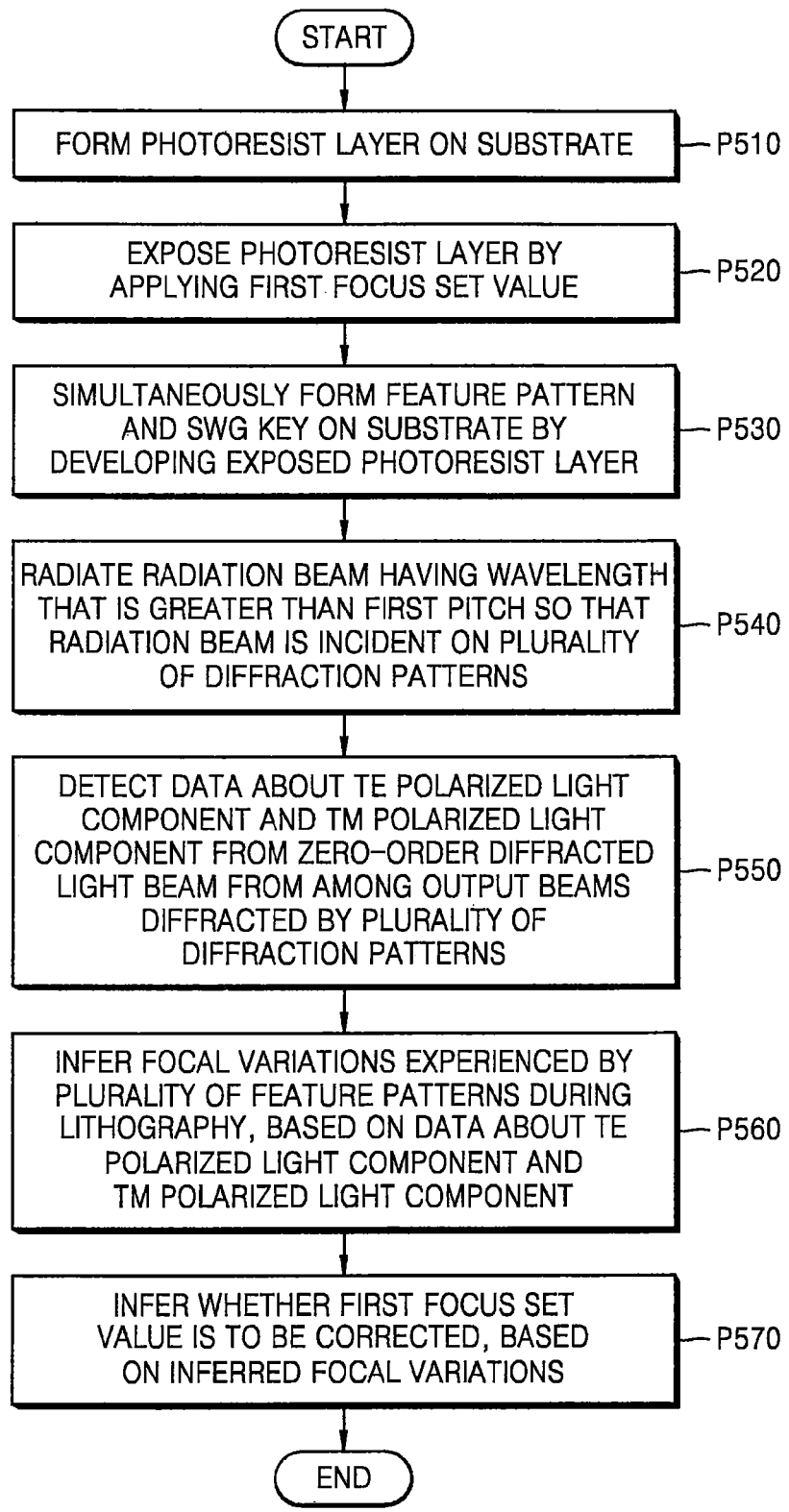
FIG. 18 is a flowchart of a method of manufacturing an integrated circuit (IC) device, according to some embodiments of the inventive concept.

FIG. 18 is a flowchart of a method of manufacturing an IC device, according to some embodiments of the inventive concept.

Referring to FIG. 18, in operation P510, a photoresist layer is formed on a substrate.

The substrate may be a semiconductor wafer. In some embodiments, the substrate may include a semiconductor element, such as, silicon (Si) or germanium (Ge), or a compound semiconductor, such as, Si carbide (SiC), gallium arsenide (GaAs), indium arsenide (InAs), or indium phosphide (InP). In some embodiments, the substrate may have a silicon-on-insulator (SOI) structure. For example, the substrate may include a buried oxide (BOX) layer. In some embodiments, the substrate may include a conductive region, for example, an impurity-doped well or an impurity-doped structure. The substrate may have various isolation structures, such as, a shallow trench isolation (STI) structure. At least one selected from an insulation layer, a conductive layer, a semiconductor layer, a metal layer, a metal oxide layer, a metal nitride layer, a polymer layer may be formed on the substrate.

The photoresist layer may be formed of a resist material for EUV (13.5 nm). In other embodiments, the photoresist layer may be formed of resist for F2 excimer laser (157 nm), ArF excimer laser (193 nm), or KrF excimer laser (248 nm). The photoresist layer may be formed of positive photoresist or negative photoresist.

In operation P520, the photoresist layer is exposed by applying a first focus set value.

Although the exposure may be performed using the exposure apparatus 100 of FIG. 4, embodiments of the inventive concept are not limited thereto. The exposure may be performed using any of a variety of exposure equipment.

In operation P530, a feature pattern, and an SWG key including a plurality of diffraction patterns arranged at intervals of a first pitch may be simultaneously formed on the same level on the substrate by developing the exposed photoresist layer.

In some embodiments, in the operation P530, the plurality of feature patterns 14 and the SWG key 16 as illustrated in FIGS. 1A and 1B may be simultaneously formed on the substrate.

In other embodiments, in the operation P530, the plurality of feature patterns 14 and the SWG key 26 as illustrated in FIG. 2 may be simultaneously formed on the substrate.

In other embodiments, in the operation P530, the plurality of feature patterns 14 as illustrated in FIG. 1B and the SWG key 16 and the micro-DBO key 36 as illustrated in FIG. 3 may be simultaneously formed on the substrate.

In operation P540, a radiation beam having a wavelength that is greater than the first pitch is incident on the plurality of diffraction patterns. The radiation beam incident on the plurality of diffraction patterns may have a wavelength that is greater than the first pitch of the plurality of diffraction patterns, for example, a wavelength that is more than twice the first pitch. For example, the radiation beam may have a wavelength of about 230 to about 850 nm.

The operation P540 may be performed according to the same method as that described above with reference to operation P320 of FIGS. 6 and 11.

In operation P550, data about a TE polarized light component and a TM polarized light component, for example, a phase difference between the TE polarized light component and the TM polarized light component, is detected from a zero-order diffracted light beam from among output beams diffracted by the plurality of diffraction patterns.

In some embodiments, the data may be detected according to operation P330 described above with reference to of FIGS. 6 and 11. In other embodiments, while the data about the TE polarized light component and the TM polarized light component is being detected from the zero-order diffracted light beam from among the output beams diffracted by the plurality of diffraction patterns in operation P550, as described above with reference to operation P360 of FIG. 11, data about the intensities of ±n-order diffracted light beams (where n is an integer equal to or greater than 1) diffracted at identical angles so as to be symmetrical with each other from among output beams reflected and diffracted by a plurality of diffraction patterns constituting a micro-DBO key may be further detected, and a deviation between the intensities may be calculated.

In operation P560, focal variations experienced by the feature pattern during lithography are inferred based on the data about the TE polarized light component and the TM polarized light component detected in operation P550.

When the phase difference between the TE polarized light component and the TM polarized light component is detected from the zero-order diffracted light beam from among the output beams diffracted by the plurality of diffraction patterns included in the SWG key in operation P550, the focal variations experienced by the feature pattern during lithography are inferred based on the phase difference between the TE polarized light component and the TM polarized light component in operation P560.

When the data about the intensities of the ±n-order diffracted light beams (where n is an integer equal to or greater than 1) obtained by the plurality of diffraction patterns included in the micro-DBO key is further detected in operation P550, an overlay error of the feature pattern may be further inferred from the data about the intensities of the ±n-order diffracted light beams.

In operation P570, it is determined whether the first focus set value is to be corrected, based on the focal variations inferred in operation P560.

Figure 19:
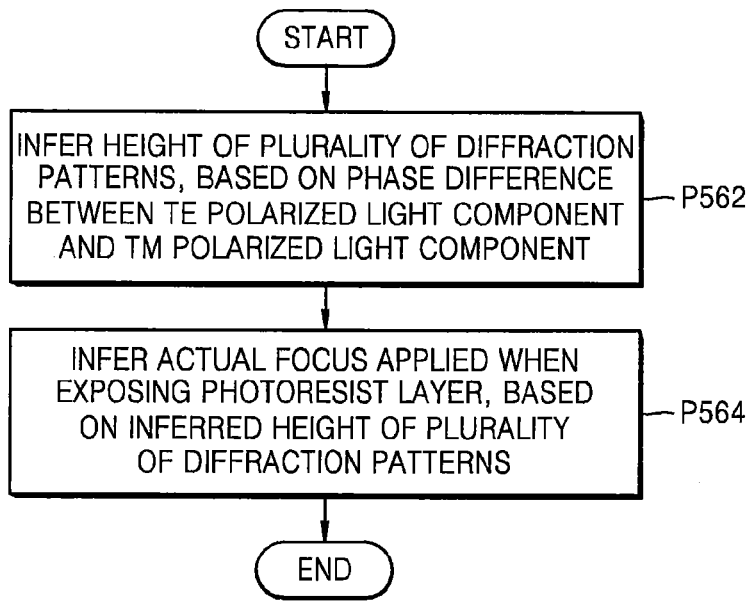
FIG. 19 is a flowchart of an exemplary operation of inferring a focal variation experienced by a feature pattern, which is included in a method of manufacturing an IC device according to some embodiments of the inventive concept.

FIG. 19 is a flowchart of an example of the operation P560 of FIG. 18 of inferring the focal variations experienced by the feature pattern.

Referring to FIG. 19, in operation P562, a height of the plurality of diffraction patterns is inferred based on the data about the TE polarized light component and the TM polarized light component detected in operation P550 of FIG. 18.

When the phase difference between the TE polarized light component and the TM polarized light component is detected from the zero-order diffracted light beam from among the output beams diffracted by the plurality of diffraction patterns in operation P550, a graph obtained based on repetitive experiments as illustrated in FIG. 9 or a similar graph thereto may be used to infer the height of the plurality of diffraction patterns in operation P562. Alternatively, the height of the plurality of diffraction patterns may be inferred in operation P562, based on an equation in which the relationship between the phase difference $\Delta\varphi$ between the TE polarized light component and the TM polarized light component and the height H of the plurality of diffraction patterns 16P is defined based, for example, on repetitive experiments by reflecting various process parameters for lithography. In some embodiments, a deterministic approach may be used to determine the height.

In operation P564, actual focus applied in operation P520 of exposing the photoresist layer is inferred based on the height of the plurality of diffraction patterns inferred in operation P562.

Alternatively, the actual focus may be inferred using the values that are set based on experimental values of correlations between the heights H of the plurality of diffraction patterns 16P and defocus aberrations as illustrated in FIGS. 7 and 8.

Figure 20:
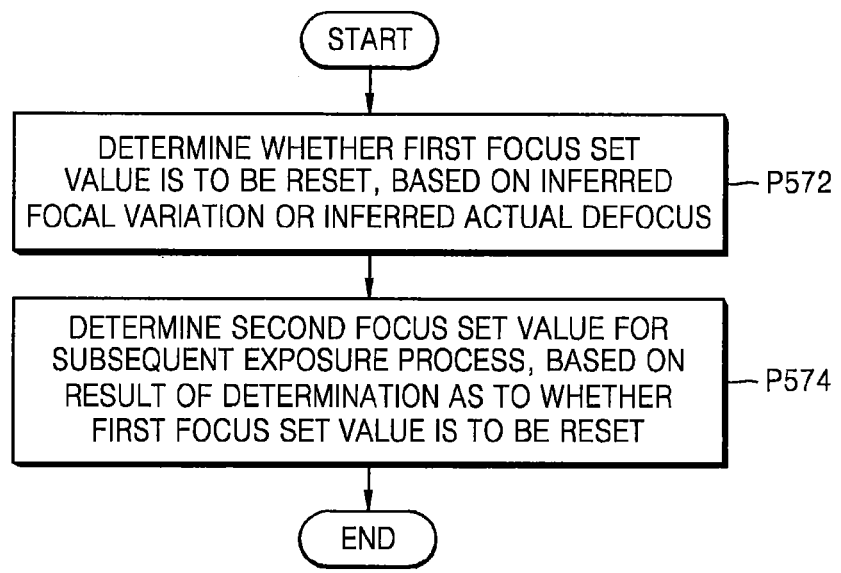
FIG. 20 is a flowchart of an exemplary operation of determining whether a first focus set value is to be corrected, which is included in a method of manufacturing an IC device according to some embodiments of the inventive concept.

FIG. 20 is a flowchart of an example of the operation P570 of FIG. 18 of determining whether the first focus set value is to be corrected.

Referring to FIG. 20, in operation P572, it is determined whether the first focus set value is to be re-set, based on the focal variations inferred in operation P560 of FIG. 18 or the actual focus inferred in operation P564 of FIG. 19.

In operation P574, a second focus set value for a subsequent exposure process is determined based on a result of the determination of operation P572.

If the focal variations inferred in operation P560 of FIG. 18 or the actual focus inferred in operation P564 of FIG. 19 is within a tolerance value, a focus set value in the subsequent exposure process may not be changed. On the other hand, if the focal variations inferred in operation P560 of FIG. 18 or the actual focus inferred in operation P564 of FIG. 19 is out of the tolerance, the second focus set value may be set to a new value capable to compensate for the inferred focal variations or the inferred actual focus.

In the method of manufacturing an IC device according to embodiments of the inventive concept described above with reference to FIGS. 18-20, when monitoring focal variations that a photoresist pattern obtained on a substrate via an exposure process and a developing process has experienced during the exposure process, a phase difference between a TE polarized light component and a TM polarized light component from among the output beams diffracted by a plurality of diffraction patterns having different heights in proportion to focusing of an exposure apparatus may be analyzed. Thus, the focal variations experienced by the photoresist pattern formed on the substrate during the exposure process may be inferred accurately. That is, focal variations of several nm may be inferred. Therefore, nondestructive in-line (or in situ) monitoring of a focus of an exposure apparatus applied during lithography for manufacturing an IC device and fine focal variations experienced during lithography may be provided.

Moreover, focal variations experienced by a plurality of feature patterns formed on the same level as the plurality of diffraction patterns may be measured using a zero-order diffracted light beam from among diffracted beams obtained by a plurality of diffraction patterns that constitute a SWG key from among the plurality of diffraction patterns obtained via the exposure process and the developing process, and an overlay error of the plurality of feature patterns may be measured using ±n-order diffracted light beams obtained by a plurality of diffraction patterns that constitute a micro-DBO key from among the plurality of diffraction patterns obtained via the exposure process and the developing process. Accordingly, focal variations and overlay errors may be simultaneously in-line (or in situ) monitored using a single substrate target in an actual product manufacturing process, leading to a reduction in metrology time.

Figure 21:
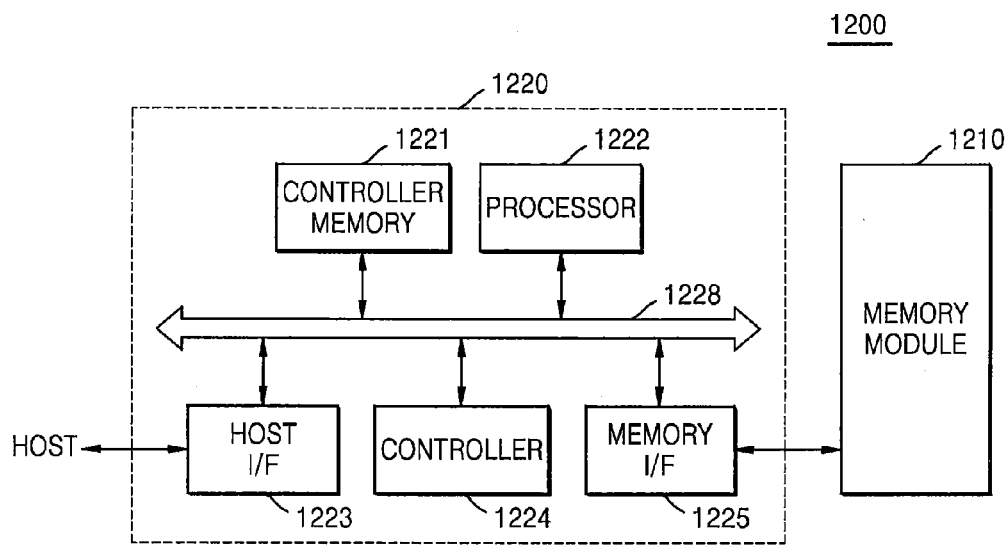
FIG. 21 is a block diagram of a memory card including an IC device fabricated using an IC device fabricating method according to some embodiments of the inventive concept.

FIG. 21 is a block diagram of a memory card 1200 including an IC device fabricated using an IC device fabricating method according to embodiments of the inventive concept.

The memory card 1200 includes a memory controller 1220 that generates command and address signals and a memory module 1210, for example, a flash memory including one or a plurality of flash memory devices. The memory controller 1220 includes a host interface (I/F) 1223 that transmits and/or receives command and address signals to/from a host, and a memory I/F 1225 that transmits and/or receives command and address signals to/from the memory module 1210. The host I/F 1223, a controller 1224, and the memory I/F 1225 communicate with a controller memory 1221, such as an SRAM, and a processor 1222, such as a central processing unit (CPU), through a common bus 1228.

The memory module 1210 receives command and/or address signals from the memory controller 1220, stores data in at least one of the memory devices of the memory module 1210 in response to the command and/or address signals, and retrieves data from at least one of the memory devices. Each memory device includes a plurality of addressable memory cells and a decoder that generates column signals and row signals to access at least one of the plurality of addressable memory cells during program and read operations.

At least one selected from the memory controller 1220 and the memory module 1210 included in the memory card 1200 and the components 1221, 1222, 1223, 1224 and 1225 included in the memory controller 1220 includes an IC device formed from a substrate target according to embodiments of the inventive concept, an IC device manufactured using a lithography metrology method according to embodiments of the inventive concept, or an IC device manufactured using an IC device manufacturing method according to embodiments of the inventive concept.

Figure 22:
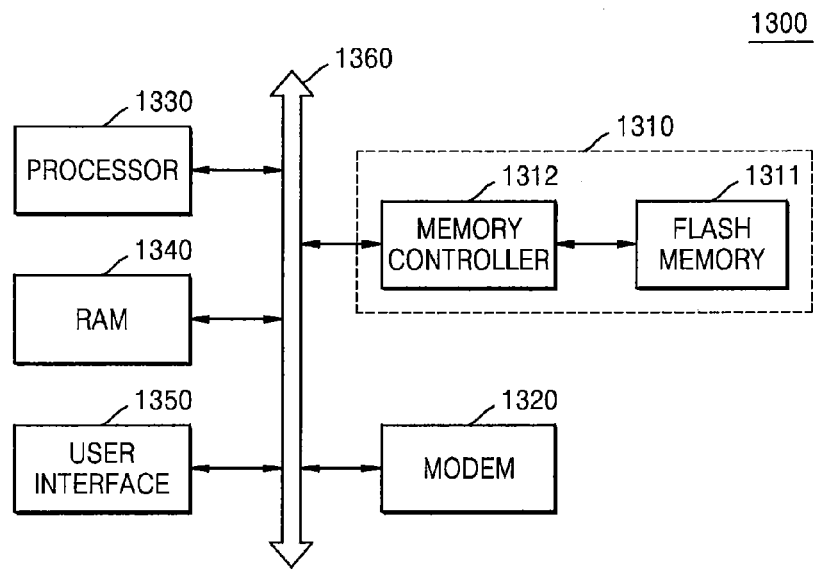
FIG. 22 is a block diagram of a memory system that employs a memory card including an IC device fabricated using an IC device fabricating method according to some embodiments of the inventive concept.

FIG. 22 is a block diagram of a memory system 1300 including a memory card 1310 including an IC device fabricated using an IC device fabricating method according to embodiments of the inventive concept.

The memory system 1300 may include a processor 1330, such as a CPU, a random access memory (RAM) 1340, a user interface 1350, and a modem 1320 that communicate with each other through a common bus 1360. Each of the components transmits a signal to the memory card 1310 and receives a signal from the memory card 1310 through the common bus 1360. At least one selected from the memory card 1310, the processor 1330, the RAM 1340, the user interface 1350, and the modem 1320 included in the memory system 1300 includes an IC device formed from a substrate target according to embodiments of the inventive concept, an IC device manufactured using a lithography metrology method according to embodiments of the inventive concept, or an IC device manufactured using an IC device manufacturing method according to embodiments of the inventive concept. The memory card 1310 includes a memory controller 1312 coupled to a flash memory 1311, which is configured to store/retrieve date associated with commands.

The memory system 1300 may be applicable to various electronic application fields. For example, the memory system 1300 may be applicable to solid state drives (SSDs), CMOS image sensors (CISs), and a computer application chipset.

The memory systems and the devices may be packaged in any of various package forms including, but not limited to, ball grid arrays (BGAs), chip scale packages (CSPs), plastic leaded chip carrier (PLCC), plastic dual in-line package (PDIP), multi chip package (MCP), wafer-level fabricated package (WFP), and wafer-level processed stack package (WSP).

As will be appreciated by one skilled in the art, aspects of the present disclosure may be illustrated and described herein in any of a number of patentable classes or contexts including any new and useful process, machine, manufacture, or composition of matter, or any new and useful improvement thereof. Accordingly, aspects of the present disclosure may be implemented entirely hardware, entirely software (including firmware, resident software, micro-code, etc.) or combining software and hardware implementation that may all generally be referred to herein as a "circuit," "module," "component," or "system." Furthermore, aspects of the present disclosure may take the form of a computer program product comprising one or more computer readable media having computer readable program code embodied thereon.

Any combination of one or more computer readable media may be used. The computer readable media may be a computer readable signal medium or a computer readable storage medium. A computer readable storage medium may be, for example, but not limited to, an electronic, magnetic, optical, electromagnetic, or semiconductor system, apparatus, or device, or any suitable combination of the foregoing. More specific examples (a non-exhaustive list) of the computer readable storage medium would include the following: a portable computer diskette, a hard disk, a random access memory (RAM), a read-only memory (ROM), an erasable programmable read-only memory (EPROM or Flash memory), an appropriate optical fiber with a repeater, a portable compact disc read-only memory (CD-ROM), an optical storage device, a magnetic storage device, or any suitable combination of the foregoing. In the context of this document, a computer readable storage medium may be any tangible medium that can contain, or store a program for use by or in connection with an instruction execution system, apparatus, or device.

A computer readable signal medium may include a propagated data signal with computer readable program code embodied therein, for example, in baseband or as part of a carrier wave. Such a propagated signal may take any of a variety of forms, including, but not limited to, electromagnetic, optical, or any suitable combination thereof. A computer readable signal medium may be any computer readable medium that is not a computer readable storage medium and that can communicate, propagate, or transport a program for use by or in connection with an instruction execution system, apparatus, or device. Program code embodied on a computer readable signal medium may be transmitted using any appropriate medium, including but not limited to wireless, wireline, optical fiber cable, RF, etc., or any suitable combination of the foregoing.

Computer program code for carrying out operations for aspects of the present disclosure may be written in any combination of one or more programming languages, including an object oriented programming language such as Java, Scala, Smalltalk, Eiffel, JADE, Emerald, C++, C#, VB.NET, Python or the like, conventional procedural programming languages, such as the "C" programming language, Visual Basic, Fortran 2003, Perl, COBOL 2002, PHP, ABAP, dynamic programming languages such as Python, Ruby and Groovy, or other programming languages. The program code may execute entirely on the user's computer, partly on the user's computer, as a stand-alone software package, partly on the user's computer and partly on a remote computer or entirely on the remote computer or server. In the latter scenario, the remote computer may be connected to the user's computer through any type of network, including a local area network (LAN) or a wide area network (WAN), or the connection may be made to an external computer (for example, through the Internet using an Internet Service Provider) or in a cloud computing environment or offered as a service such as a Software as a Service (SaaS).

Aspects of the present disclosure are described herein with reference to flowchart illustrations and/or block diagrams of methods, apparatus (systems), and computer program products according to embodiments of the disclosure. It will be understood that each block of the flowchart illustrations and/or block diagrams, and combinations of blocks in the flowchart illustrations and/or block diagrams, can be implemented by computer program instructions. These computer program instructions may be provided to a processor of a general purpose computer, server, special purpose computer, or other programmable data processing apparatus to produce a machine, such that the instructions, which execute via the processor of the computer or other programmable instruction execution apparatus, create a mechanism for implementing the functions/acts specified in the flowchart and/or block diagram block or blocks.

These computer program instructions may also be stored in a computer readable medium that when executed can direct a computer, server, other programmable data processing apparatus, or other devices to function in a particular manner, such that the instructions when stored in the computer readable medium produce an article of manufacture including instructions which when executed, cause a computer to implement the function/act specified in the flowchart and/or block diagram block or blocks. The computer program instructions may also be loaded onto a computer, server, other programmable instruction execution apparatus, or other devices to cause a series of operational steps to be performed on the computer, other programmable apparatuses or other devices to produce a computer implemented process such that the instructions which execute on the computer or other programmable apparatus provide processes for implementing the functions/acts specified in the flowchart and/or block diagram block or blocks.

While the inventive concept has been particularly shown and described with reference to exemplary embodiments thereof, it will be understood that various changes in form and details may be made therein without departing from the spirit and scope of the following claims.

What is claimed:

1. A substrate target for lithography metrology comprising:
   a substrate;
   a feature pattern on the substrate; and
   a Sub Wavelength Grating (SWG) key on a same level relative to the substrate as the feature pattern, the SWG key comprising a plurality of diffraction patterns spaced apart at a first pitch that is configured to measure a focal variation affecting formation of the feature pattern,
   wherein the plurality of diffraction patterns are within a one-time measurement spot, formed by one shot of a radiation beam projected onto the substrate,
   wherein the SWG key is configured to measure the focal variation based on a height of the plurality of diffraction patterns, and
   wherein the height of the plurality of diffraction patterns is determined based on a phase difference between a transverse electric (TE) polarized radiation component and a transverse magnetic (TM) polarized radiation component included in a zero-order diffracted light beam diffracted by the plurality of diffraction patterns.

2. The substrate target for lithography metrology of claim 1, wherein the SWG key and the feature pattern comprise the same material.

3. The substrate target for lithography metrology of claim 1, wherein the first pitch is less than a wavelength of a radiation beam used to measure the focal variation.

4. The substrate target for lithography metrology of claim 1, wherein each of the diffraction patterns has a rectangular cross-sectional shape.

5. The substrate target for lithography metrology of claim 1, wherein each of the diffraction patterns has inclined sidewalls.

6. A substrate target for lithography metrology comprising:
   a micro-Diffraction Based Overlay (micro-DBO) key on a substrate, wherein the micro-DBO key comprises a plurality of first diffraction patterns each having a first width as a minimum width; and
   a SubWavelength Grating (SWG) key on the substrate, wherein the SWG key comprises a plurality of second diffraction patterns each having a second width that is less than the first width,
   wherein the plurality of first diffraction patterns and the plurality of second diffraction patterns are within a one-time measurement spot, formed by one shot of a radiation beam projected onto the substrate, wherein the SWG key is configured to measure a focal variation affecting formation of a plurality of feature patterns based on a height of the plurality of second diffraction patterns, and wherein the height of the plurality of second diffraction patterns is determined based on a phase difference between a transverse electric (TE) polarized radiation component and a transverse magnetic (TM) polarized radiation component included in a zero-order diffracted light beam diffracted by the plurality of second diffraction patterns.

7. The substrate target for lithography metrology of claim 6, wherein:
the micro-DBO key is located within a first area on the substrate, and
the SWG key is located in a second area of the substrate within the first area and is surrounded by the plurality of first diffraction patterns.

8. The substrate target for lithography metrology of claim 6, wherein:
the micro-DBO key is configured to measure an overlay error of a plurality of feature patterns on the substrate, and
the SWG key is configured to measure a focal variation affecting formation of the plurality of feature patterns.

9. The substrate target for lithography metrology of claim 8, wherein:
the second diffraction patterns have respective line shapes that are parallel to each other, and
the second diffraction patterns and the feature patterns are the same material.

10. A substrate comprising:
a feature pattern included in an integrated circuit on the substrate; and
an in-situ metrology pattern spaced apart from the feature pattern on the substrate,
wherein the in-situ metrology pattern and the feature pattern are both configured to have equal heights relative to a surface of the substrate,
wherein the in-situ metrology pattern is within a one-time measurement spot, formed by one shot of a radiation beam projected onto the substrate,
wherein the in-situ metrology pattern is configured to measure a focal variation based on a height of the in-situ metrology pattern, and
wherein the height of the in-situ metrology pattern is determined based on a phase difference between a transverse electric (TE) polarized radiation component and a transverse magnetic (TM) polarized radiation component included in a zero-order diffracted light beam diffracted by the in-situ metrology pattern.

11. The substrate of claim 10, wherein the in-situ metrology pattern and the feature pattern are both lithographically configured to have the equal heights relative to the surface of the substrate.

12. The substrate of claim 10, wherein the in-situ metrology pattern and the feature pattern are commonly formed on the substrate.

13. The substrate of claim 10, wherein the in-situ metrology pattern comprises a SubWavelength Grating (SWG) key comprising a plurality of diffraction patterns spaced apart at a first pitch on the substrate that is configured to measure focal variation affecting formation of the feature pattern.

14. The substrate of claim 13, wherein the first pitch is less than a wavelength of a radiation beam configured to measure the focal variation.

15. The substrate of claim 14, wherein the plurality of diffraction patterns comprises a first plurality of diffraction patterns each having a first width, the substrate further comprising:
a micro-Diffraction Based Overlay (micro-DBO) key on the substrate, the micro-DBO key comprising a plurality of second diffraction patterns each having a second width that is greater than the first width.

16. The substrate of claim 15, wherein the micro-DBO key is configured to indicate an overlay error associated with formation of the feature pattern responsive to the radiation beam.

17. The substrate of claim 15, wherein the SWG key is surrounded by separate ones of the plurality of second diffraction patterns included in the micro-DBO key.

* * * * *